(12) United States Patent
Soutschek

(10) Patent No.: US 8,580,521 B2
(45) Date of Patent: Nov. 12, 2013

(54) **DEVICE FOR SEROLOGICALLY DETECTING *YERSINIA* INFECTIONS AND/OR SECONDARY DISEASES THEREOF AND USE OF THE PROTEINS MYFA AND PSAA OF *Y. ENTEROCOLITICA* AND *Y. PSEUDOTUBERCULOSIS* AS RECOMBINANT ANTIGENS**

(75) Inventor: Erwin Soutschek, Berg (DE)

(73) Assignee: Mikrogen GmbH, Neuried (DE)

( * ) Notice: Subject to any disclaimer, the term of this patent is extended or adjusted under 35 U.S.C. 154(b) by 0 days.

(21) Appl. No.: 13/148,439

(22) PCT Filed: Feb. 11, 2010

(86) PCT No.: PCT/EP2010/051673
§ 371 (c)(1),
(2), (4) Date: Aug. 8, 2011

(87) PCT Pub. No.: WO2010/092093
PCT Pub. Date: Aug. 19, 2010

(65) Prior Publication Data
US 2011/0306515 A1    Dec. 15, 2011

(30) Foreign Application Priority Data
Feb. 16, 2009 (EP) ..................................... 09002105

(51) Int. Cl.
*G01N 33/53* (2006.01)
*C07K 7/04* (2006.01)

(52) U.S. Cl.
USPC .......................................... 435/7.1; 530/300

(58) Field of Classification Search
None
See application file for complete search history.

(56) References Cited

PUBLICATIONS

Iriarte, et al., "Molecular Determinants of *Yersinia* Pathogenesis," Microbiologia, vol. 12 (2), pp. 267-270 (1996).
Tomaso, et al., "Seroprevalence of Anti-*Yersinia* Antibodies in Healthy Austrians," European Journal of Epidemiology, vol. 21 (1), pp. 77-81 (2006).
Stolk-Engelaar, et al., "Clinical Presentation and Diagnosis of Gastrointestinal Infections by *Yersinia enterocolitica* in 261 Dutch Patients," Scandinavian Journal of Infectious Diseases, vol. 28 (6), pp. 571-575 (1996).
Heesemann, J., "Enterpathogenic *Yersinias*: Pathogenicity Factors and New Diagnostic Methods," Imunitat Und Infektion, vol. 18 (6), pp. 186-191 (1990).
Leiva, et al., "Coagglutination with Antisera to MyfA and PsaA to distinguish *Yersinia enterocolitica* from *Yersinia pseudotuberculosis* Pathogenic Isolates," Contributions to Microbiology and Imunology; Yersiniosis: Pesent and Future, pp. 158-164 (1994).
Iushchuk, et al., "Laboratory Diagnosis of *Yersinia* Infection and its Improvement," Zhurnal Mikrobiologii, Epidemiologii, I Immunobiologii, (3), pp. 61-66 (2007).
Devdariani, et al., "Enzme Immunoassay System for Identification of Typical and Atypical Strains of Plague Microbe," Medicinskaa Parazitologia I Parazitarnye Bolenzni, (1), pp. 31-33 (1997).
Robins-Brown, et al., "*Yersinia* Species," International Handbook of Foodborne Pathogens, pp. 323-356 (2003).
Gomes-Solecki, et al., "LcrV Capture Enzyme-Linked Immunosorbent Assay for Detection of *Yersinia pestis* from Human Samples," Clinical and Diagnostic Laboratory Immunology, vol. 12 (2), pp. 339-346 (2005).
Heesemann, et al., "Analysis of the Class-specific Immune Response to *Yersinia enterocolitica* Virulence-associated Antigens in Orogastrically Infected Rabbits," Microbial Pathogenesis, vol. 5 (6), pp. 437-447 (1988).
Hensel, et al., "The Prevalence of Anti-*Yersinia* Outer Protein Antibodies in Bavarian Slaughter Pigs," Berliner Und Muenchener Tieraerztliche Wochenschrift, vol. 117 (1-2), pp. 30-38 (2004).
Benner, et al., "Immune Response to *Yersinia* Outer Proteins and Other *Yersinia pestis* Antigens After Experimental Plague Infection in Mice," Infection and Immunity, vol. 67 (4), pp. 1922-1928 (1999).
Chen et al. *Microbes and Infection*, vol. 8 (2006), pp. 2501-2508.
Chen et al. *Microbes and Infection*, vol. 8 (2006), Supplementary Tables S1-S3, pp. 1-5.
UNIPROTKB Search Results for blastp: "*Yersinia*" (3 pages), dated Jul. 31, 2012.

*Primary Examiner* — Nancy T Vogel
(74) *Attorney, Agent, or Firm* — Chalin A. Smith; Smith Patent Consulting

(57) ABSTRACT

Devices are disclosed for serologically detecting an infection with human-pathogenic *Yersinia* ssp, wherein said device comprises at least one antigen selected from the group of antigens consisting of the following group: YopD, YopH, YopM, YopE, V-AG and YopN or a fragment of one of said antigens having at least eight consecutive amino acids and furthermore one of two proteins selected from MyfA and PsaA or fragments of one of said two proteins having at least eight consecutive amino acids.

12 Claims, 9 Drawing Sheets

Fig. 1. Representation of the homologous amino acid sequence regions of the MyfA and PsaA antigens. The homologous regions (consensus) are marked black. A line is drawn round the N- and C-terminal homologous regions.
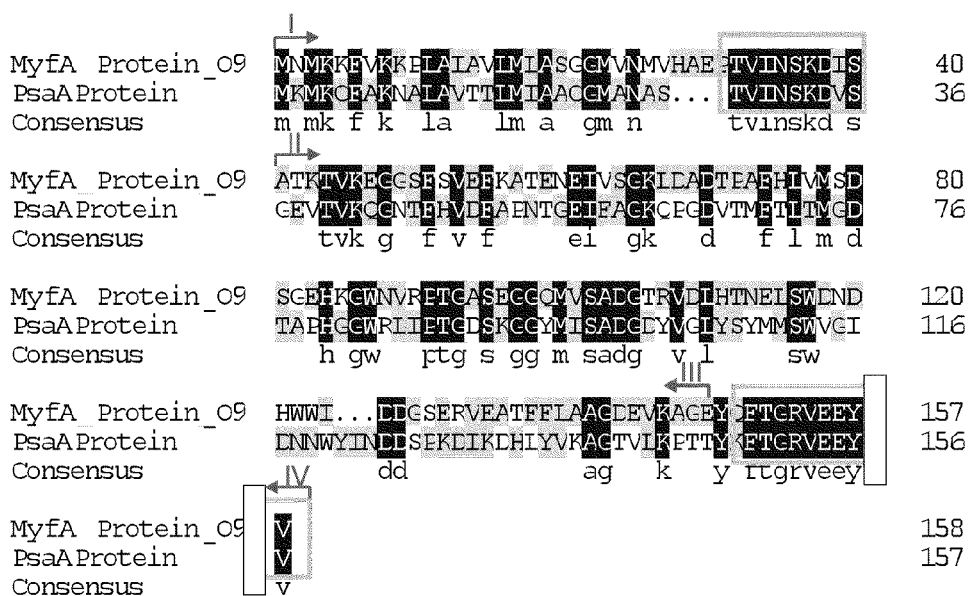

Fig. 2. *In silico* determination of the antigenic domains of MyfA and PsaA. The antigenicity index was calculated on the basis of the Jameson-Wolf algorithm and the hydrophilicity of the antigen was calculated on the basis of the Kyte-Doolittle algorithm. The leader sequence is marked with a black arrow.
MyfA
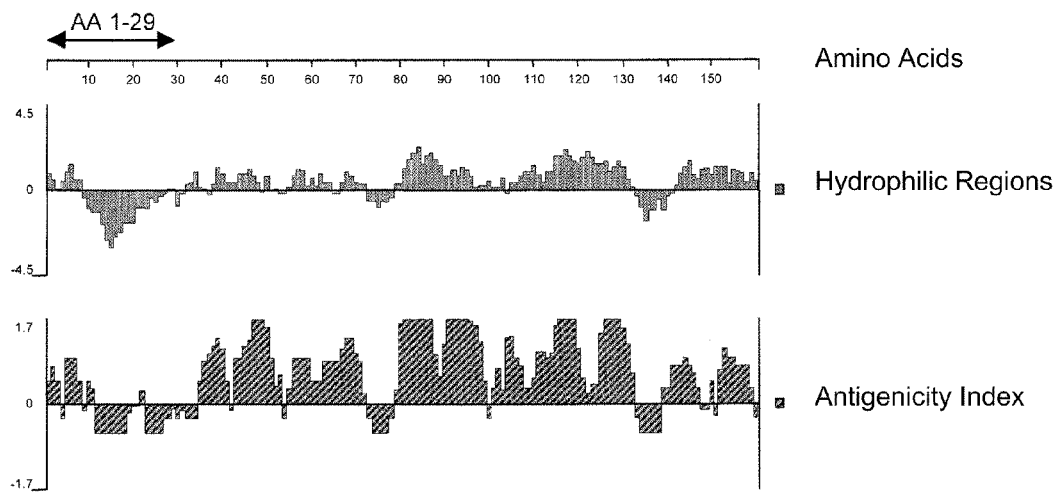
PsaA
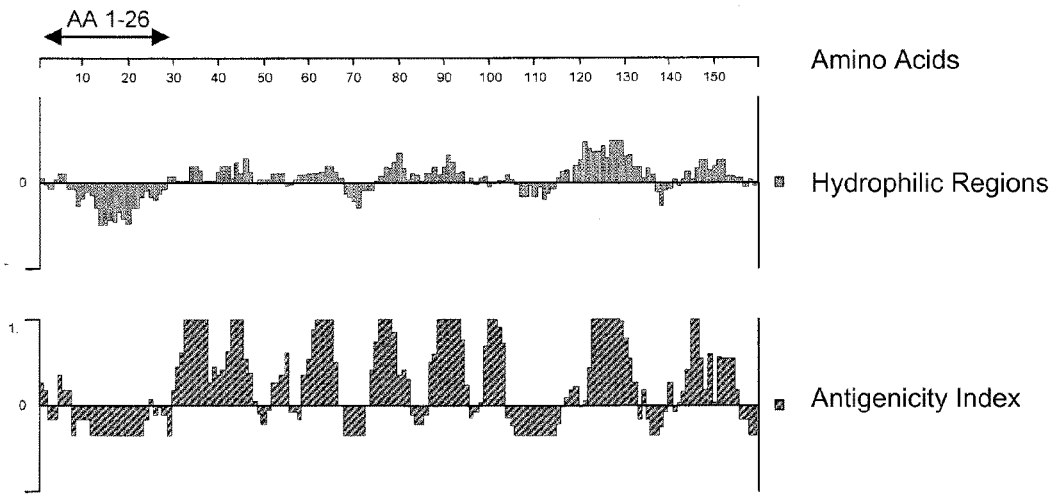

Fig. 3. Schematic representation of the DNA sequences (Examples 1, 2 and 3) of the four His-Tag-MyfA fusion proteins used. The primer sequences used for amplification are marked with arrows (I, II, III, IV). The leader sequences are shown in light-grey and the regions homologous with PsaA are shown in white.
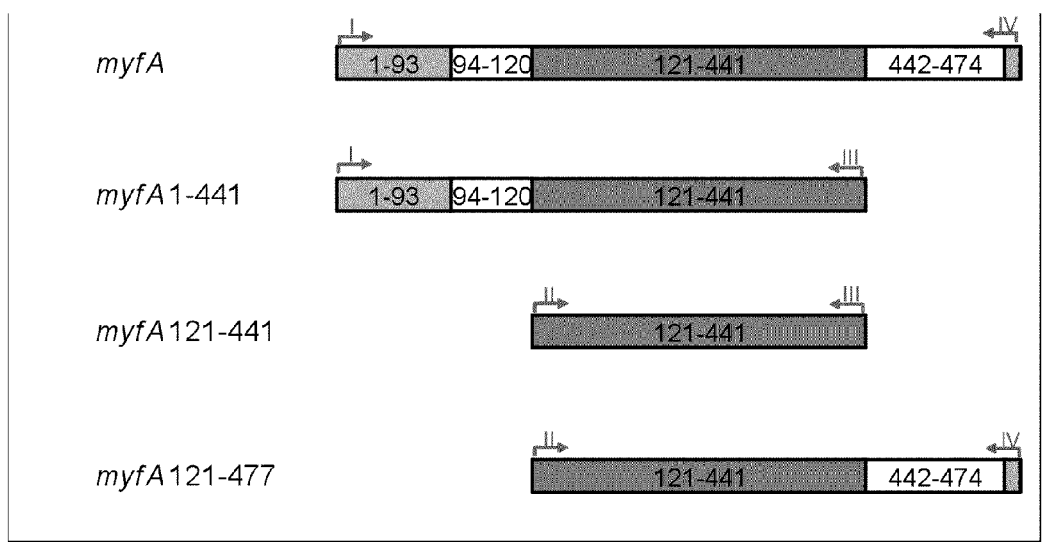

Fig. 4. Chromatographic separation (SDS-polyacrylamide-gel electrophoresis) of the MyfA partial fragments *myfA* 1-441, *myfA* 121-441 and *myfA* 121-447 (Fig. 3) with subsequent Coomassie Blue staining (left) and immunoblot (*myfA*, *myfA* 1-441, *myfA* 121-441 and *myfA* 121-447; Fig. 3) with anti-*Y. enterocolitica* (O:3 or O:9) and anti-MyfA sera from rabbit (right).
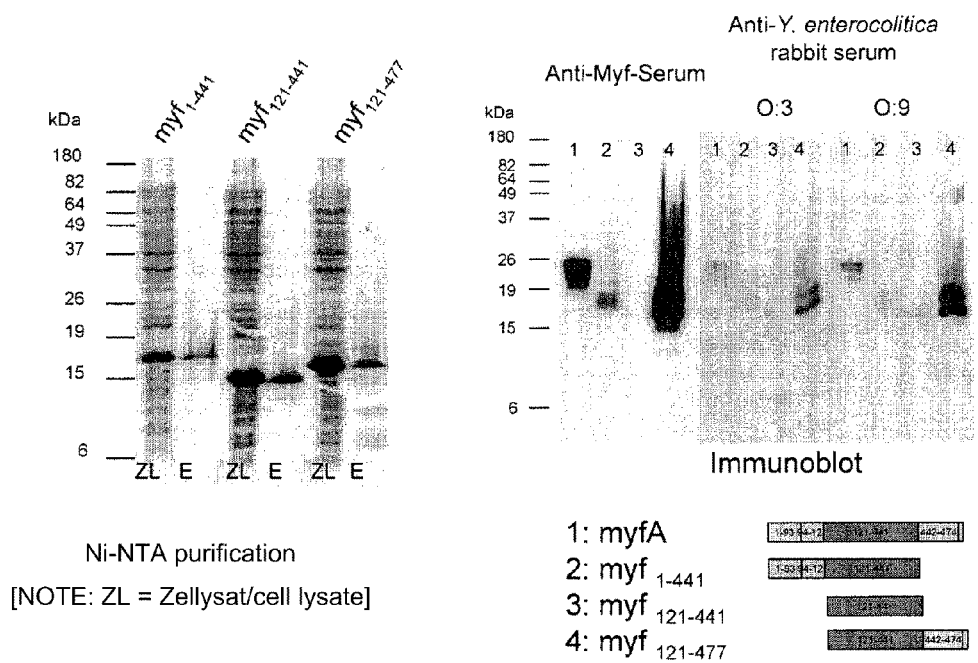

Fig. 5. Verification of the serological reactivity of the purified MyfA total protein (MyfA) and the purified MyfA partial fragments MyfA 1-441, MyfA 121-441 and MyfA 121-447 (Fig. 1; Fig. 3) by means of line-assays. The test strips were incubated with four different anti-*Y. enterocolitica* O:3, O:8 or O:9 sera from rabbit (1-4) before (*) and after infection.
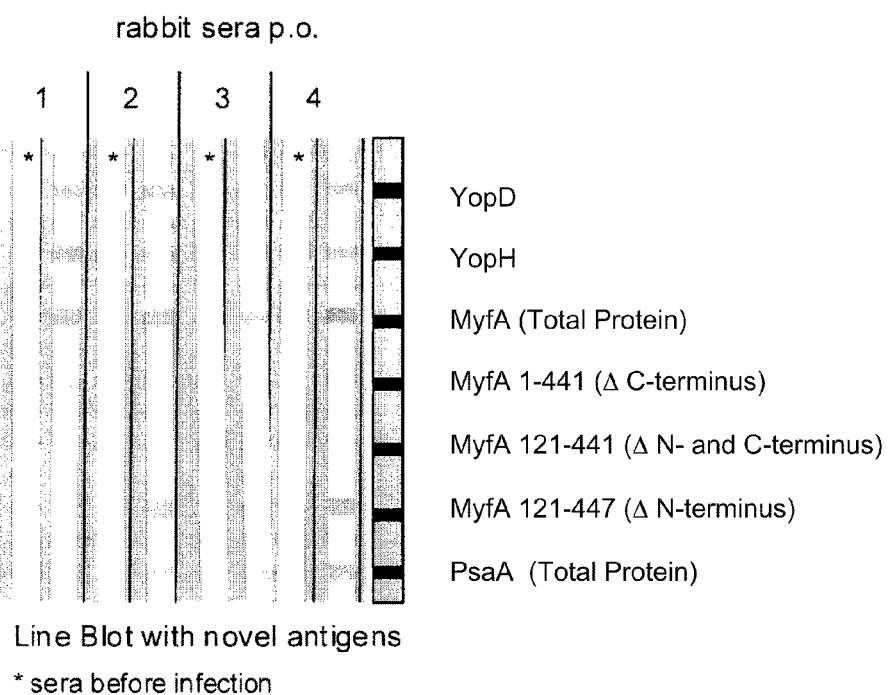

Fig. 6. Serological reactivity of human anti-*Y. enterocolitica* or anti-*Y. pseudotuberculosis* serum with YopM, YopH, V-AG, YopD, YopN, YopE, MyfA and PsaA.

LYE01: *Y. pseudotuberculosis*
LYE16: *Y. enterocolitica* (serotype O:3)

Fig. 7. IgG response to Yop, MyfA-MIK and PsaA-MIK antigens among the tested Bavarian blood donor sera (n=40).
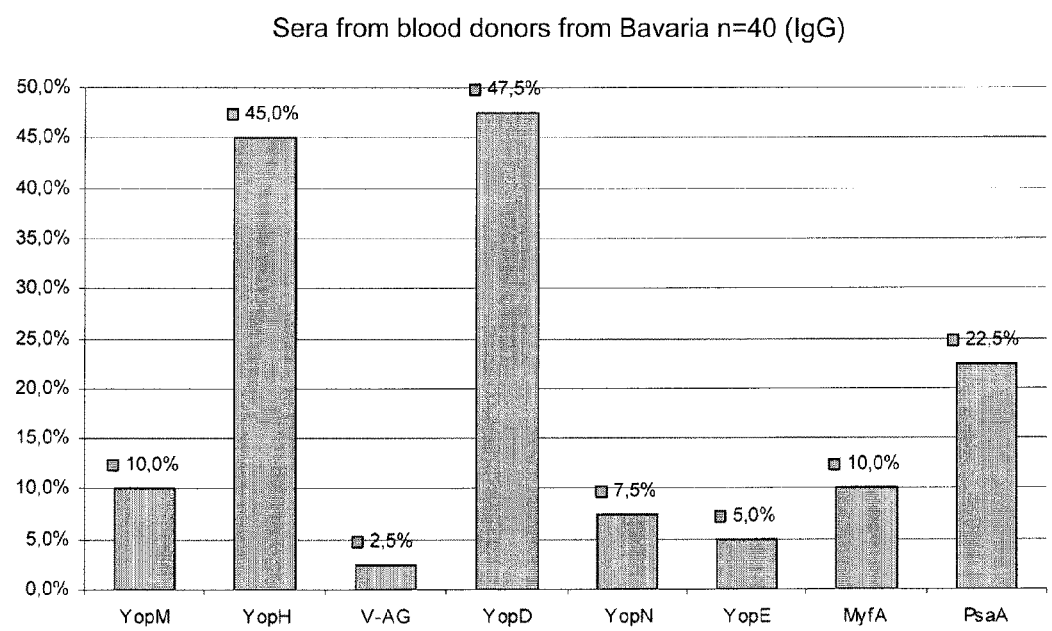

Fig. 8. IgG response to Yop, MyfA-MIK and PsaA-MIK antigens among the tested yersiniosis patient sera from Finland (n=18).
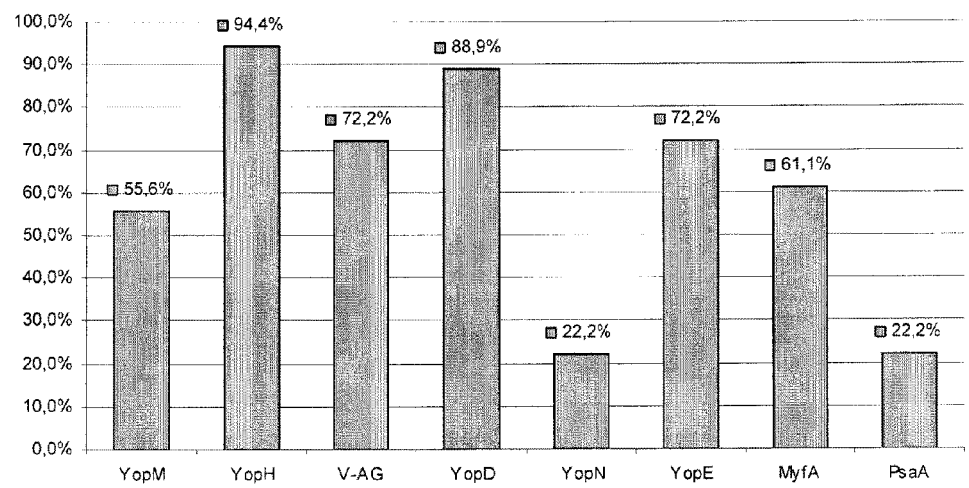

Fig. 9. IgG response to Yop, MyfA-MIK and PsaA-MIK antigens among the tested yersiniosis patient sera from Germany (n=23).
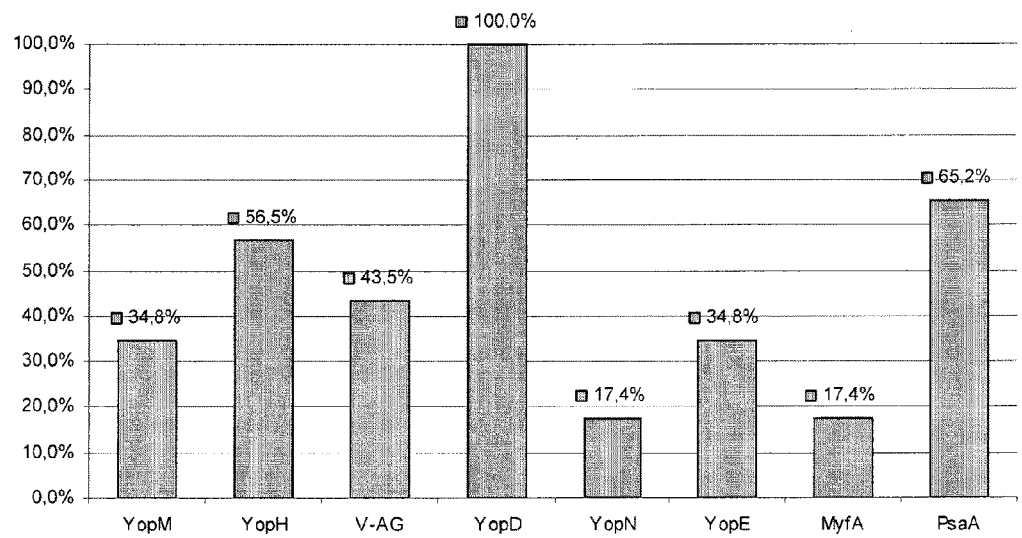

SEQUENCE LISTING

<160> NUMBER OF SEQ ID NOS: 24

<210> SEQ ID NO 1
<211> LENGTH: 306
<212> TYPE: PRT
<213> ORGANISM: Yersinia

<400> SEQUENCE: 1

```
Met Thr Ile Asn Ile Lys Thr Asp Ser Pro Ile Ile Thr Thr Gly Ser
1               5                   10                  15

Gln Ile Asp Ala Ile Thr Thr Glu Thr Val Gly Gln Ser Gly Glu Val
            20                  25                  30

Lys Lys Thr Glu Asp Thr Arg His Glu Ala Gln Ala Ile Lys Ser Ser
        35                  40                  45

Glu Ala Ser Leu Ser Arg Ser Gln Val Pro Glu Leu Ile Lys Pro Ser
    50                  55                  60

Gln Gly Ile Asn Val Ala Leu Leu Ser Lys Ser Gln Gly Asp Leu Asn
65                  70                  75                  80

Gly Thr Leu Ser Ile Leu Leu Leu Leu Glu Leu Ala Arg Lys Ala
                85                  90                  95

Arg Glu Met Gly Leu Gln Gln Arg Asp Ile Glu Asn Lys Ala Ala Ile
            100                 105                 110

Thr Ala Gln Lys Glu Gln Val Ala Glu Met Val Ser Gly Ala Lys Leu
        115                 120                 125

Met Ile Ala Met Ala Val Val Ser Gly Ile Met Ala Ala Thr Ser Thr
    130                 135                 140

Val Ala Ser Ala Phe Ser Ile Ala Lys Glu Val Lys Ile Val Lys Gln
145                 150                 155                 160

Glu Gln Ile Leu Asn Ser Asn Ile Ala Gly Arg Asp Gln Leu Ile Asp
                165                 170                 175

Thr Lys Leu Gln Gln Met Ser Asn Thr Ser Asp Lys Ala Val Ser Arg
            180                 185                 190

Glu Asp Ile Gly Arg Ile Trp Lys Pro Glu Gln Val Ala Asp Gln Asn
        195                 200                 205

Lys Leu Ala Leu Leu Asp Lys Glu Phe Arg Met Thr Asp Ser Lys Ala
```

```
                    210                 215                 220
Asn Ala Phe Asn Ala Ala Thr Gln Pro Leu Gly Gln Met Ala Asn Ser
225                 230                 235                 240

Ala Ile Gln Val His Arg Gly Tyr Ser Gln Ala Glu Val Lys Glu Lys
                245                 250                 255

Glu Val Asn Ala Ser Ile Ala Ala Asn Glu Lys Gln Lys Ala Glu Glu
            260                 265                 270

Ala Met Asn Tyr Asn Asp Asn Phe Met Lys Asp Val Leu Arg Leu Ile
        275                 280                 285

Glu Gln Tyr Val Ser Ser His Thr His Ala Met Lys Ala Ala Phe Gly
    290                 295                 300

Val Val
305

<210> SEQ ID NO 2
<211> LENGTH: 468
<212> TYPE: PRT
<213> ORGANISM: Yersinia

<400> SEQUENCE: 2

Met Asn Leu Ser Leu Ser Asp Leu His Arg Gln Val Ser Arg Leu Val
1               5                   10                  15

Gln Gln Glu Ser Gly Asp Cys Thr Gly Lys Leu Arg Gly Asn Val Ala
            20                  25                  30

Ala Asn Lys Glu Thr Thr Phe Gln Gly Leu Thr Ile Ala Ser Gly Ala
        35                  40                  45

Arg Glu Ser Glu Lys Val Phe Ala Gln Thr Val Leu Ser His Val Ala
    50                  55                  60

Asn Ile Val Leu Thr Gln Glu Asp Thr Ala Lys Leu Leu Gln Ser Thr
65                  70                  75                  80

Val Lys His Asn Leu Asn Asn Tyr Glu Leu Arg Ser Val Gly Asn Gly
                85                  90                  95

Asn Ser Val Leu Val Ser Leu Arg Ser Asp Gln Met Thr Leu Gln Asp
            100                 105                 110

Ala Lys Val Leu Leu Glu Ala Ala Leu Arg Gln Glu Ser Gly Ala Arg
        115                 120                 125

Gly His Val Ser Ser His Ser His Ser Val Leu His Ala Pro Gly Thr
    130                 135                 140

Pro Val Arg Glu Gly Leu Arg Ser His Leu Asp Pro Arg Thr Pro Pro
145                 150                 155                 160

Leu Pro Pro Arg Glu Arg Pro His Thr Ser Gly His His Gly Ala Gly
                165                 170                 175

Glu Ala Arg Ala Thr Ala Pro Ser Thr Val Ser Pro Tyr Gly Pro Glu
            180                 185                 190

Ala Arg Ala Glu Leu Ser Ser Arg Leu Thr Thr Leu Arg Asn Thr Leu
        195                 200                 205

Ala Pro Ala Thr Asn Asp Pro Arg Tyr Leu Gln Ala Cys Gly Gly Glu
    210                 215                 220

Lys Leu Asn Arg Phe Arg Asp Ile Gln Cys Cys Arg Gln Thr Ala Val
225                 230                 235                 240

Arg Ala Asp Leu Asn Ala Asn Tyr Ile Gln Val Gly Asn Thr Arg Thr
                245                 250                 255

Ile Ala Cys Gln Tyr Pro Leu Gln Ser Gln Leu Glu Ser His Phe Arg
            260                 265                 270

Met Leu Ala Glu Asn Arg Thr Pro Val Leu Ala Val Leu Ala Ser Ser
```

```
            275                 280                 285
Ser Glu Ile Ala Asn Gln Arg Phe Gly Met Pro Asp Tyr Phe Arg Gln
        290                 295                 300
Ser Gly Thr Tyr Gly Ser Ile Thr Val Glu Ser Lys Met Thr Gln Gln
305                 310                 315                 320
Val Gly Leu Gly Asp Gly Ile Met Ala Asp Met Tyr Thr Leu Thr Ile
                325                 330                 335
Arg Glu Ala Gly Gln Lys Thr Ile Ser Val Pro Val His Val Gly
            340                 345                 350
Asn Trp Pro Asp Gln Thr Ala Val Ser Ser Glu Val Thr Lys Ala Leu
        355                 360                 365
Ala Ser Leu Val Asp Gln Thr Ala Glu Thr Lys Arg Asn Met Tyr Glu
    370                 375                 380
Ser Lys Gly Ser Ser Ala Val Ala Asp Asp Ser Lys Leu Arg Pro Val
385                 390                 395                 400
Ile His Cys Arg Ala Gly Val Gly Arg Thr Ala Gln Leu Ile Gly Ala
                405                 410                 415
Met Cys Met Asn Asp Ser Arg Asn Ser Gln Leu Ser Val Glu Asp Met
            420                 425                 430
Val Ser Gln Met Arg Val Gln Arg Asn Gly Ile Met Val Gln Lys Asp
        435                 440                 445
Glu Gln Leu Asp Val Leu Ile Lys Leu Ala Glu Gly Gln Gly Arg Pro
    450                 455                 460
Leu Leu Asn Ser
465

<210> SEQ ID NO 3
<211> LENGTH: 293
<212> TYPE: PRT
<213> ORGANISM: Yersinia

<400> SEQUENCE: 3

Met Thr Thr Leu His Asn Ile Ser Tyr Gly Asn Thr Thr Leu Arg Asn
1               5                   10                  15
Glu His Pro Glu Thr Ala Ser Ser Gln Ile Val Asn Gln Thr Leu Gly
            20                  25                  30
Gln Phe Arg Gly Glu Ser Val Gln Ile Val Ser Gly Thr Leu Gln Ser
        35                  40                  45
Ile Ala Asp Met Ala Glu Glu Val Thr Phe Val Phe Ser Glu Arg Lys
    50                  55                  60
Glu Leu Ser Leu Asp Lys Arg Lys Leu Ser Asp Ser Gln Ala Arg Val
65                  70                  75                  80
Ser Asp Val Glu Glu Val Asn Gln Tyr Leu Ser Lys Val Pro Glu
                85                  90                  95
Leu Glu Gln Lys Gln Asn Val Ser Glu Leu Leu Ser Leu Leu Ser Asn
            100                 105                 110
Ser Pro Asn Ile Ser Leu Ser Gln Leu Lys Ala Tyr Leu Glu Gly Lys
        115                 120                 125
Ser Glu Glu Pro Ser Glu Gln Phe Lys Met Leu Cys Gly Leu Arg Asp
    130                 135                 140
Ala Leu Lys Gly Arg Pro Glu Leu Ala His Leu Ser His Leu Val Glu
145                 150                 155                 160
Gln Ala Leu Val Ser Met Ala Glu Glu Gln Gly Glu Ala Ile Val Leu
                165                 170                 175
Gly Ala Arg Ile Thr Pro Glu Ala Tyr Arg Glu Ser Gln Ser Ser Val
```

```
                            180                 185                 190
Asn Pro Leu Gln Pro Leu Arg Asp Thr Tyr Arg Asp Ala Val Met Gly
            195                 200                 205

Tyr Gln Gly Ile Tyr Ala Ile Trp Ser Asp Leu Gln Lys Arg Phe Pro
        210                 215                 220

Asn Gly Asp Ile Asp Ser Val Ile Leu Phe Leu Gln Lys Ala Leu Ser
225                 230                 235                 240

Ala Asp Leu Gln Ser Gln Gln Ser Gly Ser Gly Arg Glu Lys Leu Gly
                245                 250                 255

Ile Val Ile Ser Asp Leu Gln Lys Leu Lys Glu Phe Gly Ser Val Ser
            260                 265                 270

Asp Gln Val Lys Gly Phe Trp Gln Phe Phe Ser Glu Gly Lys Thr Asn
        275                 280                 285

Gly Val Arg Pro Phe
    290

<210> SEQ ID NO 4
<211> LENGTH: 220
<212> TYPE: PRT
<213> ORGANISM: Yersinia

<400> SEQUENCE: 4

Met Pro Lys Ile Ser Ser Phe Ile Ser Thr Ser Leu Pro Leu Pro Thr
1               5                   10                  15

Ser Val Ser Gly Ser Ser Ser Val Gly Glu Met Ser Gly Arg Ser Val
            20                  25                  30

Ser Gln Gln Lys Ser Glu Gln Tyr Ala Asn Asn Leu Ala Gly Arg Thr
        35                  40                  45

Glu Ser Pro Gln Gly Ser Ser Leu Ala Ser Arg Ile Thr Glu Lys Leu
    50                  55                  60

Ser Ser Met Ala Arg Ser Ala Ile Glu Phe Ile Lys Arg Met Phe Ser
65                  70                  75                  80

Glu Gly Ser His Lys Pro Val Val Thr Pro Ala Pro Thr Pro Ala Gln
                85                  90                  95

Met Pro Ser Pro Thr Ser Phe Ser Asp Ser Ile Lys Gln Leu Ala Ala
            100                 105                 110

Glu Thr Leu Pro Lys Tyr Ile Gln Gln Leu Ser Ser Leu Asp Ala Glu
        115                 120                 125

Thr Leu Gln Lys Asn His Asp Gln Phe Ala Thr Gly Ser Gly Pro Leu
    130                 135                 140

Arg Gly Ser Ile Thr Gln Cys Gln Gly Leu Met Gln Phe Cys Gly Gly
145                 150                 155                 160

Glu Leu Gln Ala Glu Ala Ser Ala Ile Leu Asn Thr Pro Val Cys Gly
                165                 170                 175

Ile Pro Phe Ser Gln Trp Gly Thr Ile Gly Gly Ala Ala Ser Ala Tyr
            180                 185                 190

Val Ala Ser Gly Val Asp Leu Thr Gln Ala Ala Asn Glu Leu Lys Gly
        195                 200                 205

Leu Ala Gln Gln Met His Gln Leu Leu Ser Leu Met
    210                 215                 220

<210> SEQ ID NO 5
<211> LENGTH: 505
<212> TYPE: PRT
<213> ORGANISM: Yersinia

<400> SEQUENCE: 5
```

```
Met Phe Ile Asn Pro Arg Asn Val Ser Asn Thr Phe Leu Gln Glu Pro
1               5                  10                  15

Leu Arg His Ser Ser Asp Leu Thr Glu Ile Pro Val Glu Ala Glu Asn
            20                  25                  30

Val Lys Ser Lys Thr Glu Tyr Tyr Asn Ala Trp Ser Glu Trp Glu Arg
            35                  40                  45

Asn Ala Pro Pro Gly Asn Gly Glu Gln Arg Glu Met Ala Val Ser Arg
            50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Arg Leu
                85                  90                  95

Val Ala Ser Cys Asn Ser Leu Thr Glu Leu Pro Glu Leu Pro Gln Ser
                100                 105                 110

Leu Lys Ser Leu Glu Val Tyr Glu Asn Asn Leu Lys Ala Leu Pro Asp
            115                 120                 125

Leu Pro Pro Leu Leu Val Asp Leu Arg Val Phe Asn Asn Gln Leu Glu
        130                 135                 140

Glu Leu Pro Glu Leu Gln Asn Leu Pro Phe Leu Thr Glu Ile Tyr Ala
145                 150                 155                 160

Asn Asn Asn Ser Leu Lys Thr Leu Pro Asp Leu Pro Pro Ser Leu Val
                165                 170                 175

Asp Leu Asn Val Arg Glu Asn Tyr Leu Thr Ala Leu Pro Glu Leu Pro
            180                 185                 190

Gln Ser Leu Ile Phe Leu Asp Ile Ser Asp Asn Ile Leu Ser Gly Leu
        195                 200                 205

Ser Glu Leu Pro Pro Asn Leu Ser Cys Leu Asp Ala Ser Arg Asn Gly
    210                 215                 220

Ile Arg Ser Leu Cys Asp Leu Pro Pro Ser Leu Val Tyr Leu Asp Val
225                 230                 235                 240

Arg Asp Asn Gln Leu Ile Glu Leu Pro Ala Leu Pro Ser Gly Leu Glu
            245                 250                 255

Arg Leu Ile Ala Ser Phe Asn His Leu Ala Glu Leu Pro Glu Leu Pro
            260                 265                 270

Pro Asn Leu Tyr Tyr Leu Asp Ala Ser Arg Asn Glu Ile Ser Ser Leu
        275                 280                 285

Cys Asp Leu Pro Pro Ser Leu Val Asp Leu Asn Val Arg Lys Asn Gln
    290                 295                 300

Leu Ile Glu Leu Pro Ala Leu Pro Pro Asp Leu Glu Arg Leu Ile Ala
305                 310                 315                 320

Ser Phe Asn His Leu Ala Glu Leu Pro Glu Leu Pro Pro Asn Leu Ser
            325                 330                 335

Tyr Leu Asp Ala Ser Arg Asn Glu Ile Ser Ser Leu Cys Asp Leu Pro
            340                 345                 350

Pro Ser Leu Val Asp Leu Asn Val Arg Lys Asn Gln Leu Ile Glu Leu
        355                 360                 365

Pro Ala Leu Pro Pro Asp Leu Glu Arg Leu Ile Ala Ser Phe Asn His
    370                 375                 380

Leu Ala Glu Leu Pro Glu Leu Pro Pro Asn Leu Ser Tyr Leu Asp Ala
385                 390                 395                 400

Ser Arg Asn Glu Ile Ser Ser Leu Cys Asp Leu Pro Pro Ser Leu Val
            405                 410                 415

Glu Leu Asp Val Arg Asp Asn Gln Leu Ile Glu Leu Pro Ala Leu Pro
```

```
                       420              425             430
Pro His Leu Glu Arg Leu Ile Ala Ser Leu Asn His Leu Ala Glu Val
         435                 440                 445

Pro Glu Leu Pro Gln Asn Leu Lys Gln Leu His Val Glu His Asn Ala
        450                  455                 460

Leu Arg Glu Phe Pro Asp Ile Pro Glu Ser Val Glu Asp Leu Arg Met
465                 470                 475                 480

Asp Ser Glu Arg Val Ile Asp Pro Tyr Glu Phe Ala His Glu Thr Ile
                485                 490                 495

Asp Lys Leu Glu Asp Asp Val Phe Glu
                500             505

<210> SEQ ID NO 6
<211> LENGTH: 333
<212> TYPE: PRT
<213> ORGANISM: Yersinia

<400> SEQUENCE: 6

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Lys Ile Asp Ile Ser Ile
            35                  40                  45

Lys Tyr Asp Pro Lys Lys Asp Ser Glu Val Phe Ala Glu Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Glu Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Lys Lys Met Pro Gln Thr Thr Ile
210                 215                 220

Lys Asp Asp Glu Leu His Glu Val Gly Val Ile Ala Gly Ala Glu Lys
225                 230                 235                 240

Gln Ile Val Ser Ile Lys Asn Phe Leu Glu Ser Glu Asn Lys Arg Thr
                245                 250                 255

Gly Ala Leu Gly Asn Leu Lys Asp Ser Tyr Ser Tyr Asn Lys Asp Asn
            260                 265                 270

Asn Glu Leu Ser His Phe Ala Thr Ala Cys Ser Asp Lys Ser Arg Pro
        275                 280                 285

Leu Asn Asp Leu Val Ser Gln Lys Thr Thr Gln Leu Ser Asp Ile Thr
```

```
                290                 295                 300
Ser Arg Phe Asn Ser Ala Ile Glu Ala Leu Asn Arg Phe Ile Gln Lys
305                 310                 315                 320

Tyr Asp Ser Val Met Gln Arg Leu Leu Asp Asp Thr Arg
                325                 330

<210> SEQ ID NO 7
<211> LENGTH: 131
<212> TYPE: PRT
<213> ORGANISM: Yersinia

<400> SEQUENCE: 7

Met Glu Pro Thr Val Ile Asn Ser Lys Asp Ile Ser Ala Thr Lys Thr
1               5                   10                  15

Val Lys Glu Gly Gly Ser Phe Ser Val Glu Phe Lys Ala Thr Glu Asn
                20                  25                  30

Glu Ile Val Ser Gly Lys Leu Asp Ala Asp Thr Pro Ala Phe His Leu
            35                  40                  45

Val Met Ser Asp Ser Gly Glu His Lys Gly Trp Asn Val Arg Pro Thr
        50                  55                  60

Gly Ala Ser Glu Gly Gly Gln Met Val Ser Ala Asp Gly Thr Arg Val
65                  70                  75                  80

Asp Leu His Thr Asn Glu Leu Ser Trp Asp Asn Asp His Trp Trp Ile
                85                  90                  95

Asp Asp Gly Ser Glu Arg Val Glu Ala Thr Phe Phe Leu Ala Ala Gly
                100                 105                 110

Asp Glu Val Lys Ala Gly Glu Tyr Gln Phe Thr Gly Arg Val Glu Glu
            115                 120                 125

Tyr Val Glu
    130

<210> SEQ ID NO 8
<211> LENGTH: 133
<212> TYPE: PRT
<213> ORGANISM: Yersinia

<400> SEQUENCE: 8

Met Ser Thr Val Ile Asn Ser Lys Asp Val Ser Gly Glu Val Thr Val
1               5                   10                  15

Lys Gln Gly Asn Thr Phe His Val Asp Phe Ala Pro Asn Thr Gly Glu
                20                  25                  30

Ile Phe Ala Gly Lys Gln Pro Gly Asp Val Thr Met Phe Thr Leu Thr
            35                  40                  45

Met Gly Asp Thr Ala Pro His Gly Gly Trp Arg Leu Ile Pro Thr Gly
        50                  55                  60

Asp Ser Lys Gly Gly Tyr Met Ile Ser Ala Asp Gly Asp Tyr Val Gly
65                  70                  75                  80

Leu Tyr Ser Tyr Met Met Ser Trp Val Gly Ile Asp Asn Asn Trp Tyr
                85                  90                  95

Ile Asn Asp Asp Ser Pro Lys Asp Ile Lys Asp His Leu Tyr Val Lys
                100                 105                 110

Ala Gly Thr Val Leu Lys Pro Thr Thr Tyr Lys Phe Thr Gly Arg Val
            115                 120                 125

Glu Glu Tyr Val Phe
    130

<210> SEQ ID NO 9
```

```
<211> LENGTH: 396
<212> TYPE: DNA
<213> ORGANISM: Yersinia

<400> SEQUENCE: 9
atggaaccga ctgttattaa tagtaaagac atctctgcaa caaaaactgt taaagaggga      60
ggttcgttct cagttgaatt caaggccact gaaaacgaga ttgtgtcagg caaattggat     120
gcagatacac ctgccttcca tctggtaatg tcggactcag gggaacataa aggttggaat     180
gttcggccta ccggtgcatc tgagggagga cagatggttt ctgcagatgg taccagagtt     240
gacttacata caaatgagct atcgtgggat aacgaccact ggtggataga tgacggttct     300
gagcgtgtgg aagcgacttt ctttcttgct gctggcgacg aggttaaagc aggtgaatat     360
cagttcactg gcgcgtgttga ggaatatgtc gagtaa                              396

<210> SEQ ID NO 10
<211> LENGTH: 402
<212> TYPE: DNA
<213> ORGANISM: Yersinia

<400> SEQUENCE: 10
atgtctactg tcattaactc caaggatgtt tctggtgagg tgactgtcaa gcagggaaac      60
acattccacg tcgattttgc gcctaacaca ggagagattt ttgcgggtaa acagccgggt     120
gatgtcacta tgtttacgct aactatgggt gatactgcac cacacggtgg ttggcgtttg     180
attccaacag gggactcaaa aggtggatat atgatcagcg ccgatggtga ctatgttggt     240
ttatacagtt atatgatgtc atgggtaggt atagataata actggtatat aaatgatgac     300
tctcctaaag atataaaaga tcatctgtac gttaaggcag ggactgtcct taaaccaacg     360
acttataaat tcacggggcg tgttgaagag tatgtatttt aa                        402

<210> SEQ ID NO 11
<211> LENGTH: 159
<212> TYPE: PRT
<213> ORGANISM: Yersinia

<400> SEQUENCE: 11

Met Asn Met Lys Lys Phe Val Lys Lys Pro Leu Ala Ile Ala Val Leu
1               5                   10                  15

Met Leu Ala Ser Gly Gly Met Val Asn Met Val His Ala Glu Pro Thr
            20                  25                  30

Val Ile Asn Ser Lys Asp Ile Ser Ala Thr Lys Thr Val Lys Glu Gly
        35                  40                  45

Gly Ser Phe Ser Val Glu Phe Lys Ala Thr Glu Asn Glu Ile Val Ser
    50                  55                  60

Gly Lys Leu Asp Ala Asp Thr Pro Ala Phe His Leu Val Met Ser Asp
65                  70                  75                  80

Ser Gly Glu His Lys Gly Trp Asn Val Arg Pro Thr Gly Ala Ser Glu
                85                  90                  95

Gly Gly Gln Met Val Ser Ala Asp Gly Thr Arg Val Asp Leu His Thr
            100                 105                 110

Asn Glu Leu Ser Trp Asp Asn Asp His Trp Trp Ile Asp Asp Gly Ser
        115                 120                 125

Glu Arg Val Glu Ala Thr Phe Phe Leu Ala Ala Gly Asp Glu Val Lys
    130                 135                 140

Ala Gly Glu Tyr Gln Phe Thr Gly Arg Val Glu Glu Tyr Val Glu
145                 150                 155
```

<210> SEQ ID NO 12
<211> LENGTH: 158
<212> TYPE: PRT
<213> ORGANISM: Yersinia

<400> SEQUENCE: 12

```
Met Lys Met Lys Cys Phe Ala Lys Asn Ala Leu Ala Val Thr Thr Leu
1               5                   10                  15
Met Ile Ala Ala Cys Gly Met Ala Asn Ala Ser Thr Val Ile Asn Ser
            20                  25                  30
Lys Asp Val Ser Gly Glu Val Thr Val Lys Gln Gly Asn Thr Phe His
        35                  40                  45
Val Asp Phe Ala Pro Asn Thr Gly Glu Ile Phe Ala Gly Lys Gln Pro
    50                  55                  60
Gly Asp Val Thr Met Phe Thr Leu Thr Met Gly Asp Thr Ala Pro His
65                  70                  75                  80
Gly Gly Trp Arg Leu Ile Pro Thr Gly Asp Ser Lys Gly Gly Tyr Met
                85                  90                  95
Ile Ser Ala Asp Gly Asp Tyr Val Gly Leu Tyr Ser Tyr Met Met Ser
            100                 105                 110
Trp Val Gly Ile Asp Asn Asn Trp Tyr Ile Asn Asp Ser Pro Lys
        115                 120                 125
Asp Ile Lys Asp His Leu Tyr Val Lys Ala Gly Thr Val Leu Lys Pro
    130                 135                 140
Thr Thr Tyr Lys Phe Thr Gly Arg Val Glu Glu Tyr Val Phe
145                 150                 155
```

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
gtaattccat atgaatatga aaaaatttgt                                    30

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
gtaatcccat atggcaacaa aaactgt                                       27

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
ttactcgagt tcacctgctt taac                                          24

<210> SEQ ID NO 16
<211> LENGTH: 28
<212> TYPE: DNA
<213> ORGANISM: Artificial Sequence
<220> FEATURE:

```
<223> OTHER INFORMATION: primer

<400> SEQUENCE: 16
atctactcga gctcgacata ttcctcaa                                    28

<210> SEQ ID NO 17
<211> LENGTH: 38
<212> TYPE: PRT
<213> ORGANISM: Artificial Sequence
<220> FEATURE:
<223> OTHER INFORMATION: primer

<400> SEQUENCE: 17

Cys Ala Cys Ala Thr Ala Thr Gly Gly Ala Ala Cys Cys Gly Ala Cys
 1               5                  10                  15

Thr Gly Thr Thr Ala Thr Thr Ala Ala Thr Ala Gly Thr Ala Ala Ala
            20                  25                  30

Gly Ala Cys Ala Thr Cys
        35

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
atggatcctt actcgacata ttcctcaaca cg                               32

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
gccatatgtc tactgtcatt aactccaagg atg                              33

<210> SEQ ID NO 20
<211> LENGTH: 34
<212> TYPE: DNA
<213> ORGANISM: Artificial Sequence
<220> FEATURE:
<223> OTHER INFORMATION: primer

<400> SEQUENCE: 20
caggatcctt aaaatacata ctcttcaaca cgcc                             34

<210> SEQ ID NO 21
<211> LENGTH: 396
<212> TYPE: DNA
<213> ORGANISM: Yersinia

<400> SEQUENCE: 21
atggaaccga ctgttattaa tagtaaagac atctctgcaa caaaaactgt taaag

```
cagttcactg ggcgtgttga ggaatatgtc gagtaa                            396
```

```
<210> SEQ ID NO 22
<211> LENGTH: 402
<212> TYPE: DNA
<213> ORGANISM: Yersinia

<400> SEQUENCE: 22
atgtctactg tcattaactc caaggatgtt tctggtgagg tgactgtcaa gcagggaaac    60
acattccacg tcgattttgc gcctaacaca ggagagattt ttgcgggtaa acagccgggt   120
gatgtcacta tgtttacgct aactatgggt gatactgcac cacacggtgg ttggcgtttg   180
attccaacag gggactcaaa aggtggatat atgatcagcg ccgatggtga ctatgttggt   240
ttatacagtt atatgatgtc atgggtaggt atagataata actggtatat aaatgatgac   300
tctcctaaag atataaaaga tcatctgtac gttaaggcag ggactgtcct taaaccaacg   360
acttataaat tcacggggcg tgttgaagag tatgtatttt aa                      402

<210> SEQ ID NO 23
<211> LENGTH: 131
<212> TYPE: PRT
<213> ORGANISM: Yersinia

<400> SEQUENCE: 23

Met Glu Pro Thr Val Ile Asn Ser Lys Asp Ile Ser Ala Thr Lys Thr
1               5                   10                  15

Val Lys Glu Gly Gly Ser Phe Ser Val Glu Phe Lys Ala Thr Glu Asn
            20                  25                  30

Glu Ile Val Ser Gly Lys Leu Asp Ala Asp Thr Pro Ala Phe His Leu
        35                  40                  45

Val Met Ser Asp Ser Gly Glu His Lys Gly Trp Asn Val Arg Pro Thr
    50                  55                  60

Gly Ala Ser Glu Gly Gly Gln Met Val Ser Ala Asp Gly Thr Arg Val
65                  70                  75                  80

Asp Leu His Thr Asn Glu Leu Ser Trp Asp Asn Asp His Trp Trp Ile
                85                  90                  95

Asp Asp Gly Ser Glu Arg Val Glu Ala Thr Phe Phe Leu Ala Ala Gly
            100                 105                 110

Asp Glu Val Lys Ala Gly Glu Tyr Gln Phe Thr Gly Arg Val Glu Glu
        115                 120                 125

Tyr Val Glu
    130

<210> SEQ ID NO 24
<211> LENGTH: 133
<212> TYPE: PRT
<213> ORGANISM: Yersinia

<400> SEQUENCE: 24

Met Ser Thr Val Ile Asn Ser Lys Asp Val Ser Gly Glu Val Thr Val
1               5                   10                  15

Lys Gln Gly Asn Thr Phe His Val Asp Phe Ala Pro Asn Thr Gly Glu
            20                  25                  30

Ile Phe Ala Gly Lys Gln Pro Gly Asp Val Thr Met Phe Thr Leu Thr
        35                  40                  45

Met Gly Asp Thr Ala Pro His Gly Gly Trp Arg Leu Ile Pro Thr Gly
    50                  55                  60
```

-continued

```
Asp Ser Lys Gly Gly Tyr Met Ile Ser Ala Asp Gly Asp Tyr Val Gly
65              70              75              80

Leu Tyr Ser Tyr Met Met Ser Trp Val Gly Ile Asp Asn Asn Trp Tyr
                85              90              95

Ile Asn Asp Asp Ser Pro Lys Asp Ile Lys Asp His Leu Tyr Val Lys
            100             105             110

Ala Gly Thr Val Leu Lys Pro Thr Thr Tyr Lys Phe Thr Gly Arg Val
            115             120             125

Glu Glu Tyr Val Phe
    130
```

DEVICE FOR SEROLOGICALLY DETECTING YERSINIA INFECTIONS AND/OR SECONDARY DISEASES THEREOF AND USE OF THE PROTEINS MYFA AND PSAA OF Y. ENTEROCOLITICA AND Y. PSEUDOTUBERCULOSIS AS RECOMBINANT ANTIGENS

This application corresponds to the national phase of International Application No. PCT/EP2010/051673 filed Feb. 11, 2010, which, in turn, claims priority to European Patent Application No. 09.002105.6 filed Feb. 16, 2009, the contents of which are incorporated by reference herein in their entirety.

The genus *Yersinia* comprises three human-pathogenic *Yersinia* spp., *Y. pestis*, *Y. pseudotuberculosis* and *Y. enterocolitica* and eight further species namely *Y. aldovae*, *Y. bercovieri*, *Y. frederiksenii*, *Y. intermedia*, *Y. kristensenii*, *Y. mooларetti*, *Y. rohdei* and *Y. ruckeri*, which rather play a role in humans as opportunistic pathogens in the case of wounds and sepsis. *Y. pestis* causes plague and can be transmitted by fleas from the natural rodent reservoir to humans. *Y. enterocolitica* and *Y. pseudotuberculosis* occur in wild and domesticated animals in the temperate to subtropical zones throughout the world. In Germany, the intestinal disease caused by *Y. enterocolitica* and *Y. pseudotuberculosis*, called yersiniosis, is, after salmonellosis (*Salmonella enterica*) and campylobacter enteritis (*Campylobacter jejuni*), the third most common bacterial enteritis disease notified annually to the Robert Koch Institute (RKI) in Berlin. In Germany, 4987 cases of diseases caused by *Yersinia* according to the RKI disease classification were reported to the Robert Koch Institute in 2007, and 5162 in the year 2006. The highest age-specific incidence was observed in young children in the age range from 1 to 4 years (RKI). However, the actual frequency of these diseases is not known exactly—many who become ill do not see a doctor if the disease course is subclinical or mild and brief, many diseases are not clarified aetiologically and not all diagnosed cases are reported. It is estimated that up to 43% of blood donors in Germany and 31% of blood donors in Finland have specific antibodies to *Yersinia* (tested by enzyme immunoassays or immunoblots). This result suggests an unexpectedly high prevalence of yersinioses experienced in industrial countries with high standards of hygiene.

The enteropathogenic *Y. enterocolitica* and *Y. pseudotuberculosis* pathogens occur in pigs, sheep, bovines and poultry and enter food (e.g. raw pork) and drinking water mainly via the slaughtering process. Furthermore, cases of transmission to pets have been described. It has also been found that up to 100% of wild boar carry *Yersinia enterocolitica* in the nasopharyngeal cavity. *Yersinia* are able to multiply at low temperatures (>4° C.). In the industrial countries, multiplication in refrigerated foods represents the epidemiologically most important form of distribution of *Y. enterocolitica* and *Y. pseudotuberculosis*.

The exact infective dose is not known (presumably >10000 bacteria). The incubation time is two to five days after infection. Enteropathogenic *Y. enterocolitica* and *Y. pseudotuberculosis* strains generally colonise the intestine-associated lymphatic tissue of the terminal ileum, in the so-called Peyer's patches (continuous aggregation of lymphatic follicles). Following colonisation, the *Yersinia* overcome, via so-called M cells in the follicle-associated epithelial cell layer of the Peyer's patches, the gastrointestinal barrier of the organism and spread via the draining lymphatic vessels in the mesenteric lymph nodes. *Y. enterocolitica* then attacks and damages further regions of the intestine, which explains the typical tissue damage of the small intestine and colon in yersiniosis patients. *Y. pseudotuberculosis* shows a course of infection similar to that of *Y. enterocolitica*, except that mesenteric lymph nodes, liver and spleen are more often affected and enteritis symptoms and excretion via the intestine are much less than with *Y. enterocolitica*.

The enteritic form of *Yersinia* infections, also called yersiniosis, is limited, in uncomplicated cases, to the gastrointestinal tract and is characterised by watery diarrhoea for several days (called acute *Yersinia gastroenteritis*). However, depending on patients' age, immune status, histocompatibility type (HLA-B27) and sex, yersinioses can display different courses and symptoms, for example fever, nausea, colic-like lower abdominal pains (pseudoappendicitis), muscular pains and headaches and inflammations in the pharyngeal region (pharyngitis), in the mesenteric lymph nodes (acute mesenteric lymphadenitis) and in the ileum and colon (Yersinia ileitis and colitis). In uncomplicated cases, the disease abates after a few days or at the latest after two weeks.

In patients with underlying diseases, for example diabetes mellitus, liver cirrhosis, iron storage diseases (dialysis patients, thalassaemia) or immunosuppression, extraintestinal infections may occur (e.g. septic forms). Not uncommonly, septic shock with high lethality (approx. 75%) occurs after blood transfusion with *Yersinia*-contaminated banked blood.

Apart from the intestinal and extraintestinal forms of yersiniosis, in which the causative agent can generally be isolated, in up to 30% of cases there are also concomitant or secondary diseases, generally with an aseptic course. The most common secondary disease is HLA-B27-associated reactive arthritis [abbreviation: ReA] (about 60-80% of ReA cases are HLA-B27-positive). ReA starts approx. 1-4 weeks after onset of the intestinal symptoms (but often without preceding intestinal symptoms). Most often it is the joints of the lower extremities that are affected. In most cases the symptoms abate after approx. 3-12 months, but a chronic or relapsing course may also develop. Other complications that often occur after yersiniosis are inflammations of the thyroid (thyroiditis), of the heart muscle (myocarditis) and of the kidneys (glomerulonephritis), reddening of the skin (erythema) of the lower extremities (Erythema nodosum) and acute or chronic enlargement of the lymph nodes (lymphadenopathies) or of the spleen (splenomegaly).

In yersinioses without further immunological complications, for example reactive arthritis, the symptoms generally abate after a short time. Therefore in most cases it is unnecessary to treat a *Yersinia* infection with antibiotics. In the case of a septic course or persistent symptoms, differential treatment with antibiotics is necessary. Owing to the frequently occurring beta-lactamases with *Yersinia*, infections with *Y. enterocolitica* or *Y. pseudotuberculosis* are treated pathogen-specifically with gyrase inhibitors, tetracycline, trimethoprim/sulfamethoxazole etc.

Related *Yersinia* species (e.g. *Y. enterocolitica* and *Y. pseudotuberculosis*) are differentiated biochemically. *Y. pseudotuberculosis* forms a biochemically uniform group, which is divided into eight serogroups, of which the serovars I, II and III are of importance in human medicine in Europe (Bottone, [1997] Clin. Microbiol. Rev., 10, 257-276). In contrast, *Y. enterocolitica* is an extremely heterogeneous species both biochemically and serologically, with pathogenic and non-pathogenic, geographically separate subgroups. *Y. enterocolitica* is divided into six biovars (BV)/biotypes with different biochemical effects (1A, 1B, 2, 3, 4, 5) and approx. 60 serovars (with different O and H antigens) (Wauters et al., [1987] Contrib. Microbiol. Immunol., 9, 14-21). Whereas biovar 1A *Yersinia* mainly occur in the environment, the known human-pathogenic *Y. enterocolitica* strains belong to BV 1B (serotypes O:8, O:4, O:13, O:18, O:20, O:21, occurring mainly in the USA), BV 2 (Europe [O:9], USA, Japan [O:5, 27]), BV 3 (O:9 and O:5, 27) and BV 4 (Europe and USA [O:3]). (Bucher et al., [2008] Foodborne Pathog. Dis., 5, 273-280). Approximately 80-90% of reported cases of *Yersinia* gastroenteritis in Germany are caused by *Y. enterocolitica* serotype O:3 (RKI).

The virulence of the enteropathogenic *Yersinia* (*Y. enterocolitica* biovars 1B, 2, 3, 4 and 5, *Y. pseudotuberculosis*) and of the plague-causing *Y. pestis* is due to a highly conserved virulence plasmid pYV with a size of 65-70 kb (in *Y. pestis* pCDI). These virulence factors enable pathogenic *Yersinia* to survive in the host's lymphoid tissue. The *Y. enterocolitica* biovar 1A does not carry a pYV plasmid and is therefore regarded as non-pathogenic.

The pYV plasmid codes for the membrane protein YadA (*Yersinia* adhesin) and a number of so-called *Yersinia* outer proteins (Yops) and the associated secretory apparatus (T3SS), which is called Ysc (Yop secretion). As substrate of T3SS, the Yops are injected as anti-host effectors into eukaryotic cells (e.g. in macrophages). The protein complex of T3SS consists of 27 proteins with known or unknown functions, for example a regulatory function (YopQ, YopN), translocation function (YopB, YopD) and effector function (YopH, YopE, YopT, YopP, YopO). The adhesin YadA is also encoded on the virulence plasmid. It mediates the adhesion of the pathogens on host cells and enables the Yops to inject into the target cells. The so-called V antigen (LcrV) is also encoded on the pYV plasmid. This antigen forms the tip of the Ysc injectisome, regulates Yop secretion and modulation of the host's immune system.

The virulence of the *Yersinia* is also influenced by chromosomally encoded factors, in addition to the plasmid-encoded virulence factors. Adhesion of *Yersinia* on epithelial cells of the intestine requires among other things the presence of the invasin Inv and of the adhesin Ail (the "attachment invasion locus" of *Y. enterocolitica*), which can be expressed by all enteropathogenic *Yersinia*.

Other known chromosomally encoded pathogenicity factors are e.g. the secreted and thermally stable enterotoxin Yst, the so-called "mucoid *Yersinia* factor" MyfA of *Y. enterocolitica*, or the homologous pH 6 antigen PsaA of *Y. pseudotuberculosis* and *Y. pestis*, the yersiniabactin-siderophore system encoded on the so-called high-pathogenicity island (HPI) (FyuA receptor with Irp1-9), the Ysa Type-III secretory apparatus, the lipopolysaccharide LPS that is characteristic of all Gram-negative bacteria, the enzyme urease and the toxin complex TC that is active against insects (tcbA, tcaC, tccC).

The MyF fibril system consists of the three subunits MyfA, MyfB and MyfC. The fibril is constructed from MyfA subunits, whereas MyfB and MyfC form the transport and structuring apparatus. The MyfA surface antigen with a size of approx. 17 kDa is expressed in vitro during the early stationary growth phase, and full expression only takes place at 37° C. in an acid environment (pH 6). The myfA gene is present in human-pathogenic *Y. enterocolitica* strains (e.g. O:3, O:4, O:8; O:9) and in approx. 16% of non-human-pathogenic *Y. enterocolitica* BV 1A strains and shows a significant link to virulence. Leiva et al. showed, in coagglutination experiments with sera from rabbits that had been immunised intravenously with live *Y. enterocolitica* or *Y. pseudotuberculosis* strains, that the antisera obtained against MyfA (*Y. enterocolitica*) or PsaA (*Y. pseudotuberculosis*) allow bacteriological differentiation between *Y. enterocolitica* (MyfA) and *Y. pseudotuberculosis* (PsaA) strains (Leiva et al., Contrib. Microbiol. Immunol., 13, 158-164). These immunisation experiments also show that MyfA or PsaA are produced under laboratory conditions, i.e. under controlled nutrient conditions (growth medium) and temperature and pH conditions, and induce the production of the serum antibodies in intravenously immunised rabbits. However, a serodiagnostic application in humans is not under consideration. In particular, as the natural function of the antigens is unknown, it can also not be expected automatically that the MyfA or PsaA antigens are expressed during natural infection in the human gastrointestinal tract by pathogenic *Yersinia*. Additionally it has to be borne in mind that data from animal experiments can seldom be applied to the diagnostic situation in humans, because as is well known, the production of antibodies in animals can differ from that in humans.

The Psa-antigen complex (pH6 antigen) of enteropathogenic *Y. pseudotuberculosis* was originally characterised in the plague-causing *Y. pestis* as fimbriated structure with a diameter of 3-5 nm. The PsaA subunits are arranged on the bacteria surface by the translocation and structuring apparatus, which consists of PsaB and PsaC. The antigen domain PsaA, with a size of approx. 17 kDa, shows approx. 44-47% amino acid sequence homology with the *Y. enterocolitica*-homologous MyfA. As with MyfA, the production of PsaA in *Yersinia* is induced under laboratory conditions by temperature (37° C.) and slightly acid pH (pH 6). The PsaA deletion mutant strains of *Y. pestis* show a significantly reduced virulence in vitro and in vivo.

The observations that MyfA and PsaA antigens are expressed under laboratory conditions only at 37° C. and at acid pH, and that an immune response can be produced in laboratory mice and rabbits after infection with precultured (in vitro) *Yersinia* strains, leads to the presumption that these proteins might have a function during infection or might be expressed in the acidic environment of the intestinal tract. However, the exact functions of Myf and Psa during *Yersinia* infection, and therefore the importance of these antigens for *Yersinia* pathogenesis, are still unknown.

The classical diagnosis of the acute yersiniosis diseases is based primarily on detection of the pathogen in the stool, e.g. by means of cold enrichment, selective culture medium (e.g. so-called cefsulodin-Irgasan™-novobiocin agar culture medium [CIN-agar]), biochemical properties (e.g. so-called API E20 test; bioMerieux, Paris, France) and the detection of pathogen-specific nucleic acids (DNA) by polymerase chain reaction (PCR). Detection of the microbe in the stool may be possible for a period of 2 to 12 weeks. After the diarrhoea symptoms have subsided, *Yersinia* are typically no longer detectable in the stool.

Serology, i.e. detection of the individual serum antibody response to *Yersinia*-specific O and H antigens (so-called Widal and passive haemagglutination tests), virulence-associated proteins (e.g. by enzyme-linked immunosorbent assay [ELISA] and immunoblotting) or bacterial ultrasonicate (by means of complement-fixation reaction [CFR]), is suitable according to current standards for supplementary diagnosis of acute infection.

However, serodiagnostics is essential for clarifying secondary diseases, for example reactive arthritis, because direct detection of the pathogen, mostly after the acute infection has subsided, is not possible. The present invention relates to diagnostic devices, by means of which an infection with *Yersinia enterocolitica* can be differentiated serologically from an infection with *Yersinia pseudotuberculosis*.

In an acute *Yersinia* infection, typically the *Yersinia*-specific immunoglobulin (Ig) classes IgM, IgA and generally also IgG are detectable. In the course of infection, the specific IgM and IgA response is attenuated within 3-6 months (persistence of IgM: approx. 1-3 months and IgA: approx. 2-4 months), whereas *Yersinia*-specific IgG antibodies can persist for several years, possibly even life-long (in 80% of patients after a *Yersinia* infection). In chronic *Yersinia infection* and *Yersinia*-induced reactive arthritis, persistent IgA antibodies can be detected for years, along with *Yersinia*-specific antibodies of the IgG class. The *Yersinia*-specific antibodies of the IgM class are mostly no longer detectable in secondary diseases.

The conventional serological methods of detection, such as the Widal and complement-fixation reaction directed against whole cell lysates, only possess low diagnostic sensitivity and specificity owing to cross-reactivity with a large number of human pathogens (for example *Bartonella henselae, Borrelia burgdorferi, Chlamydia pneumoniae, Rickettsia rickettsii, Escherichia coli, Brucella* spp., *Salmonella* spp.). Therefore enzyme immunoassays (ELISA) and immunoblots are currently preferred for the detection of IgG, IgA and IgM antibodies to recombinantly produced virulence-associated *Yersinia*-specific antigens (e.g. Yops and V-AG).

Existing *Yersinia* serodiagnostics is based mainly on the reaction for detecting the IgG and IgA (conditionally also IgM) response to virulence plasmid pYV secreted Yop proteins, for example YopD, YopH, YopM, YopE, V-AG and YopN. The specificity and sensitivity of these Yop antigens is, however, in need of improvement and is supplemented according to the invention with additional *Yersinia*-specific antigens.

In addition, owing to the similarity of the aetiology and of the process of infection, a subclinical course of infection or a nonspecific symptomatology and a high infection rate, it is difficult to differentiate between *Y. enterocolitica* and *Y. pseudotuberculosis* infections or secondary diseases caused by these pathogens (for example ReA or post-enteritic arthritis, myocarditis, glomerulonephritis, lymphadenopathies, splenomegaly, erythema nodosum) with the conventional diagnostic test methods. However, a method for specific serological detection (i.e. in particular differentiating between the most common human-pathogenic *Yersinia* species *Y. enterocolitica* and *Y. pseudotuberculosis*) is necessary, so as to be able to provide early and effective treatment of yersinioses or prevention of secondary diseases (i.e. adequate antibiotic therapy). The different proteins of *Y. enterocolitica* (MyfA) and *Y. pseudotuberculosis* (PsaA) can make a contribution to this.

Heesemann et al. (Microbial Pathogenesis [1988], p. 437-447) describe the immune response of orally infected rabbits to virulent (pYV plasmid) and non-virulent (no pYV plasmid) serotype O:3 strains of *Yersinia enterocolitica*, which had been precultured overnight in neutral growth medium (BHI). It is unlikely that the MyfA antigen was expressed under these conditions owing to neutral pH and the growth phase. In addition the presence of the PsaA antigen is ruled out (the authors only used *Y. enterocolitica* strains). The antigens were separated using SDS-electrophoresis and were investigated further by Western blotting. No further purification was carried out. Moreover, the authors stated that this method is rather unsuitable as such for diagnostic purposes, owing to high cross-reactivity with intestinally pathogenic *Escherichia coli* and *Salmonella* strains.

Tomaso et al. (European Journal of Epidemiology [2006], 21: 77-81) and Stolck-Engelaar et al. (Scand. J. Infect. Dis. [1996], p. 571-575) describe the seroprevalence of anti-*Yersinia* antibodies in healthy Austrians and in Dutch yersiniosis patients. Determination is carried out with a commercial Western Blot assay with the antigens Yop M, Yop H, V-Ag, Yop D and Yop E. The antigens MyfA or PsaA are not used.

The only method based on the MyfA and PsaA antigens proposed to date was described by Leiva et al., 1995. However, this related to a bacteriological detection method for identifying pathogenic *Yersinia* strains after growing the cells on an agar culture medium.

The present invention relates to a device in the broader sense for serological differentiation of an infection with *Yersinia enterocolitica* from an infection with *Yersinia pseudotuberculosis*. "Serological differentiation" in the sense of the present application means that, on the basis of a sample obtained from blood (serum, plasma), it is possible to determine by means of an immunological assay whether it is an infection caused by a strain of *Yersinia enterocolitica* or *Yersinia pseudotuberculosis*. Said device contains at least one antigen selected from a group of antigens that can be classed with the outer surface proteins or secreted proteins of *Yersinia*. At least one of these antigens must be used in the device, and it is not absolutely essential to use the complete protein—it may be perfectly sufficient to use protein fragments that have a diagnostically relevant epitope.

According to the invention, the antigens are used in essentially pure form, and this is preferably achieved by producing the antigens recombinantly rather than isolating them from cell lysate.

A fragment of one of the antigens listed below, which has at least eight consecutive amino acids, preferably at least 12, more preferably at least 20, even more preferably at least 30 consecutive amino acids and quite particularly preferably at least 50 consecutive amino acids, is sufficient. In a preferred embodiment the peptides have 10 to 30 consecutive amino acids. Each peptide/fragment has at least one diagnostically relevant epitope.

When selecting the fragments, a region is selected that contains at least one diagnostically relevant epitope. The epitope regions can be localised by standard methods known by a person skilled in the art. It is possible to determine the hydrophilicity/hydrophobicity of the protein using suitable computer programs. Hydrophilic regions are as a rule predestined to carry suitable epitopes, because in the folded protein the hydrophilic regions end up on the surface. Hydrophobic regions are more likely to be localised in the interior of the folded protein and are therefore unlikely to be involved in diagnostically relevant epitopes. The epitopes are preferably linear epitopes, but conformation epitopes can also be used advantageously.

When suitable regions have been identified, these can either be synthesised by chemical synthesis or produced by recombinant methods. These proteins or peptides can then be reacted with suitable blood, serum or plasma samples, whose aetiology has been determined with other, medical parameters. In this way, a person skilled in the art can localise suitable epitopes.

The devices according to the invention thus contain at least one antigen or a fragment of one of these antigens selected from the group consisting of antigens listed hereunder. These are the following antigens:

YopD (Seq ID No. 1)
MTINIKTDSPIITTGSQIDAITTETVGQSGEVKKTEDTRHEAQAIKSSEASLSRSQVPELIKPSQ

GINVALLSKSQGDLNGTLSILLLLLELARKAREMGLQQRDIENKAAITAQKEQVAEMVSGAKL

MIAMAVVSGIMAATSTVASAFSIAKEVKIVKQEQILNSNIAGRDQLIDTKLQQMSNTSDKAVS

REDIGRIWKPEQVADQNKLALLDKEFRMTDSKANAFNAATQPLGQMANSAIQVHRGYSQA

EVKEKEVNASIAANEKQKAEEAMNYNDNFMKDVLRLIEQYVSSHTHAMKAAFGVV.

YopH (Seq ID No. 2)
MNLSLSDLHRQVSRLVQQESGDCTGKLRGNVAANKETTFQGLTIASGARESEKVFAQTVLS

HVANIVLTQEDTAKLLQSTVKHNLNNYELRSVGNGNSVLVSLRSDQMTLQDAKVLLEAALR

QESGARGHVSSHSHSVLHAPGTPVREGLRSHLDPRTPPLPPRERPHTSGHHGAGEARAT

APSTVSPYGPEARAELSSRLTTLRNTLAPATNDPRYLQACGGEKLNRFRDIQCCRQTAVRA

DLNANYIQVGNTRTIACQYPLQSQLESHFRMLAENRTPVLAVLASSSEIANQRFGMPDYFR

QSGTYGSITVESKMTQQVGLGDGIMADMYTLTIREAGQKTISVPVVHVGNWPDQTAVSSEV

TKALASLVDQTAETKRNMYESKGSSAVADDSKLRPVIHCRAGVGRTAQLIGAMCMNDSRN

SQLSVEDMVSQMRVQRNGIMVQKDEQLDVLIKLAEGQGRPLLNS.

YopN (Seq ID No. 3)
MTTLHNISYGNTTLRNEHPETASSQIVNQTLGQFRGESVQIVSGTLQSIADMAEEVTFVFSE

RKELSLDKRKLSDSQARVSDVEEQVNQYLSKVPELEQKQNVSELLSLLSNSPNISLSQLKAY

LEGKSEEPSEQFKMLCGLRDALKGRPELAHLSHLVEQALVSMAEEQGEAIVLGARITPEAY

RESQSSVNPLQPLRDTYRDAVMGYQGIYAIWSDLQKRFPNGDIDSVILFLQKALSADLQSQ

QSGSGREKLGIVISDLQKLKEFGSVSDQVKGFWQFFSEGKTNGVRPF.

YopE (Seq ID No. 4)
MPKISSFISTSLPLPTSVSGSSSVGEMSGRSVSQQKSEQYANNLAGRTESPQGSSLASRIT

EKLSSMARSAIEFIKRMFSEGSHKPVVTPAPTPAQMPSPTSFSDSIKQLAAETLPKYIQQLSS

LDAETLQKNHDQFATGSGPLRGSITQCQGLMQFCGGELQAEASAILNTPVCGIPFSQWGTI

GGAASAYVASGVDLTQAANELKGLAQQMHQLLSLM.

YopM (Seq ID No. 5)
MFINPRNVSNTFLQEPLRHSSDLTEIPVEAENVKSKTEYYNAWSEWERNAPPGNGEQREM

AVSRLRDCLDRQAHELELNNLGLSSLPELPPHLERLVASCNSLTELPELPQSLKSLEVYENN

LKALPDLPPLLVDLRVFNNQLEELPELQNLPFLTEIYANNNSLKTLPDLPPSLVDLNVRENYL

TALPELPQSLIFLDISDNILSGLSELPPNLSCLDASRNGIRSLCDLPPSLVYLDVRDNQLIELPA

LPSGLERLIASFNHLAELPELPPNLYYLDASRNEISSLCDLPPSLVDLNVRKNQLIELPALPPD

LERLIASFNHLAELPELPPNLSYLDASRNEISSLCDLPPSLVDLNVRKNQLIELPALPPDLERLI

ASFNHLAELPELPPNLSYLDASRNEISSLCDLPPSLVELDVRDNQLIELPALPPHLERLIASLN

HLAEVPELPQNLKQLHVEHNALREFPDIPESVEDLRMDSERVIDPYEFAHETIDKLEDDVFE.

V-AG (also called LCRV)

(Seq ID No. 6)
MIRAYEQNPQHFIEDLEKVRVEQLTGHGSSVLEELVQLVKDKKIDISIKYDPKKDSEVFAERV

ITDDIELLKKILAYFLPEDAILKGGHYDNQLQNGIKRVKEFLESSPNTQWELRAFMAVMHFSL

TADRIDDDILKVIVDSMNHHGDARSKLREELAELTAELKIYSVIQAEINKHLSSSGTINIHEKSI

NLMDKNLYGYTDEEIFKASAEYKILKKMPQTTIKDDELHEVGVIAGAEKQIVSIKNFLESENKR

-continued

```
TGALGNLKDSYSYNKDNNELSHFATACSDKSRPLNDLVSQKTTQLSDITSRFNSAIEALNRFI

QKYDSVMQRLLDDTR.
```

In addition to the antigen from the first group of antigens, the device according to the invention also has at least one of two further proteins, namely either the protein MyfA and/or the protein PsaA or fragments of one of these two proteins. Once again the fragments have a minimum size of at least 8 consecutive amino acids, preferably at least 12 consecutive amino acids, more preferably at least 20, particularly preferably at least 30 and quite particularly preferably at least 50 consecutive amino acids of one of the proteins MyfA and/or PsaA.

It is preferable for the device to have the two complete proteins MyfA and PsaA or fragments thereof together, wherein the individual antigens are spatially separate from one another. The amino acid sequences of the two proteins MyfA and PsaA (without leader sequence) are shown below.

```
MyfA (132-AA)
                                                    (Seq ID No. 7)
MEPTVINSKDISATKTVKEGGSFSVEFKATENEIVSGKLDADTPAFHL

VMSDSGEHKGWNVRPTGASEGGQMVSADGTRVDLHTNELSWDNDHWWI

DDGSERVEATFFLAAGDEVKAGEYQFTGRVEEYVE.

PsaA (134-AA)
                                                    (Seq ID No. 8)
MSTVINSKDVSGEVTVKQGNTFHVDFAPNTGEIFAGKQPGDVTMFTLT

MGDTAPHGGWRLIPTGDSKGGYMISADGDYVGLYSYMMSWVGIDNNW

YINDDSPKDIKDHLYVKAGTVLKPTTYKFTGRVEEYVF.
```

The proteins MyfA or PsaA are encoded by the nucleotide sequences MyfA or PsaA shown below and can be produced recombinantly using suitable vectors and host cells.

achieved if the antigens are applied spatially separately from one another in a line-assay. However, it is also possible to apply the individual antigens on a microtitre plate, so that only one antigen is present in each well. In an alternative embodiment, in each case an antigen is applied on a type of carrier (for example spheres), so that only one antigen is bound to each carrier. As an alternative, the antigens can be applied to assay plates (microchips), wherein the individual antigens are fixed on specified points on said chips.

According to the invention, first it is determined, by reaction with at least one, or even a plurality of antigens selected from the group Yop D, Yop H, Yop M, Yop E, V-AG and/or Yop N, whether it is a *Yersinia* infection. If the result of this test is positive, it is determined, using the antigen MyfA and/or PsaA, whether the infection is caused by *Yersinia enterocolitica* or *Y. pseudotuberculosis*. The individual detection steps can be carried out either simultaneously or successively.

A device for serologically detecting an infection by *Yersinia* species is, according to the invention, in a preferred embodiment a diagnostic kit. This is to be understood as a device that is used by diagnostic laboratories for serological diagnosis. In a preferred embodiment the antigens are bound spatially separately from one another on a carrier matrix, for example wells of a microtitre plate, spheres, nitrocellulose or nylon. The antibodies (mainly of classes IgG, IgM and IgA) present in a sample from a patient (e.g. blood, serum, plasma, saliva) react with the bound antigens and so are immobilised. In a preferred embodiment these are diagnostic kits, wherein ELISA assays represent a preferred embodiment. In the case of ELISA assay kits, usually the antigen is bound to the wells of a microtitre plate. The specific antibodies present in the samples can react with the antigens. The antibodies from

```
myfA
                                                                                    (Seq ID No. 9)
atggaaccgactgttattaatagtaaagacatctctgcaacaaaaactgttaaagagggaggttcgttctcagttgaattcaaggc cactgaaaacgagattgtgtcaggcaaattggatgcagatacacctgccttccatctggtaatgtcggactcaggggaacataaa ggttggaatgttcggcctaccggtgcatctgagggaggacagatggtttctgcagatggtaccagagttgacttacatacaaatga gctatcgtgggataacgaccactggtggatagatgacggttctgagcgtgtggaagcgactttctttcttgctgctggcgacgaggtt aaagcaggtgaatatcagttcactgggcgtgttgaggaatatgtcgagtaa psaA
                                                                                    (Seq ID No. 10)
atgtctactgtcattaactccaaggatgtttctggtgaggtgactgtcaagcagggaaacacattccacgtcgattttgcgcctaaca caggagagattttttgcgggtaaacagccgggtgatgtcactatgtttacgctaactatgggtgatactgcaccacacggtggttggc gtttgattccaacaggggactcaaaaggtggatatatgatcagcgccgatggtgactatgttggtttatacagttatatgatgtcat gggtaggtatagataataactggtatataaatgatgactctcctaaagatataaaagatcatctgtacgttaaggcagggactgtcc ttaaaccaacgacttataaattcacggggcgtgttgaagagtatgtattttaa
```

The individual antigens are, according to the invention, arranged spatially separately from one another in the test device or the test kit. In the case of Western Blots, for example, the antigens can be applied in the form of bands on the carrier material, wherein the individual antigens are in each case present in a particular, well-defined band. This spatial separation of the individual antigens can also be serum or plasma, which have bound specifically to the antigens present in the wells, are as a rule detected with anti-antibodies, which carry a marker, preferably an enzyme marker.

Another preferred embodiment of the device according to the invention comprises so-called line-tests. In this case, a plurality of antigens are applied on the test strips according to a predetermined pattern. The blood samples to be investigated (sera or plasmas) are reacted with the test strips and antigen-antibody reactions are detected by enzyme-labelled antibodies and subsequent colour reaction. A conclusion can be drawn about the infection or infective agent from the specific pattern of the reactivities or colour signals.

The device according to the invention can also be an immunoblot or Western blot. In this case, the diagnostically relevant proteins are first separated according to size for example by diffusion, capillary action or electrophoresis and transferred to a carrier material, for example a nylon membrane or a nitrocellulose membrane, and fixed there. This carrier material with the proteins or protein fragments bound thereto is reacted with the patient's blood samples (serum or plasma).

The immobilised specific antibodies can for example be detected by reaction with an anti-antibody. Preferably various anti-antibodies can be used, which react either with IgG, IgM or IgA. This makes further differentiation of the immune response possible. As a rule these anti-antibodies carry a marker. This can be an enzyme, which catalyses a colour reaction, but it can also be fluorescent residues or radioactive residues. What is important is that antibodies bound to antigens can be detected with the anti-antibodies.

In another embodiment, the device according to the invention is a bead-based assay. A known commercial application of these bead-based microarrays is the Luminex-XMAB technology from Luminex Corporation (Austin, USA). This system uses microspheres (so-called beads) and evaluation is based on flow cytometry. In the case of fluorescence-labelled embodiments, the antigens according to the invention can be fixed on beads and the binding of the antibodies to the antigens is visualised with suitable labelling, e.g. fluorescence.

Another preferred embodiment of the device according to the invention relates to protein microarrays. In this case various antigens are fixed in a narrow space on a surface. As it is known which antigen is present in which place, after visualisation of the antigen-antibody reaction for example by means of a colour reaction or fluorescence labelling, it is also possible to state which antigen has reacted with the antibodies in the serum.

Usually the individual antigens are fixed in the device in such a way that after the reaction it is possible to establish with which particular antigen the antibodies present in the sample have reacted. In an ELISA assay, for example, the individual antigens are put in different cavities of the microtitre plate. In the line-assay, the antigens are sprayed on different strips of the carrier material and in the case of bead and planar microarrays the respective antigens are always applied at a defined place on the carrier or defined beads. The devices according to the invention are used for detecting human-pathogenic *Yersinia* species or subspecies. By combining different antigens, on the one hand it is possible to perform sensitive and specific detection of the pathogens and on the other hand, in a preferred embodiment a differential-diagnostic detection is also possible, wherein it is possible to distinguish between an infection caused by *Yersinia enterocolitica* and an infection with *Yersinia pseudotuberculosis*.

Another essential aspect of the present invention is also that serological detection or serological differentiation is possible when the acute *Yersinia* infection has already abated. For treating these secondary diseases it is essential to be able to determine which bacterium (*Yersinia enterocolitica* or *Yersinia pseudotuberculosis*) caused the original infection.

The device according to the invention thus has at least two different antigens, wherein one antigen is selected from the group consisting of the antigens YopD, YopH, YopM, YopE, V-AG and YopN described in more detail above. The other group comprises the antigens MyfA and PsaA.

In a particularly preferred embodiment the device comprises the antigen YopD and the antigen YopH together with either MyfA or PsaA.

In a still further preferred embodiment the device according to the invention comprises the antigens YopD, YopH, YopM and either MyfA or PsaA, the combined use of MyfA and PsaA being quite particularly preferred, however.

In a particularly preferred embodiment the device according to the invention thus has the proteins MyfA and/or PsaA or fragments thereof, as defined above, together with the following protein or protein combinations, wherein these proteins can also be in the form of fragments, as defined above. The device according to the invention has at least the protein YopD, which is preferably used together with YopH and more preferably together with YopM combined with MyfA and/or PsaA.

Another preferred embodiment comprises the proteins or fragments of YopD, YopH, YopM and YopE together with MyfA and/or PsaA.

Another preferred embodiment comprises the proteins and/or fragments of YopD, YopH, YopM, YopE, V-AG together with MyfA and/or PsaA.

Another preferred embodiment comprises a combination of proteins and/or fragments with the following designations: YopD, YopH, YopM, YopE, V-AG, YopN, and MyfA and/or PsaA.

The stated antigens can also be used in the form of fragments thereof, wherein the fragments have a serologically relevant epitope. When, according to the invention, fragments of the antigens are used, in the case of the antigen MyfA, on the one hand the N-terminal fragment with the amino acids 30-41 and on the other hand the C-terminal fragment with the amino acids 148-159 is particularly preferred. In the PsaA protein, the fragments that comprise the amino acids 27-37 (N-terminus) and 144-155 (C-terminus) are particularly preferred. In this case fragments are used which comprise this amino acid sequence and which have the sizes defined in more detail above.

The present invention thus relates to the use of an antigenic protein MyfA or a fragment thereof, as defined in more detail above, either alone or together with the antigenic protein PsaA or a fragment thereof, as defined above, for serologically detecting an infection caused by *Yersinia* or an infection caused by *Y. enterocolitica* or *Y. pseudotuberculosis*. This differentiation is clinically important, because an infection caused by *Yersinia enterocolitica* can be treated differently from an infection caused by *Yersinia pseudotuberculosis*.

With the device according to the invention, it is possible to detect *Yersinia*, which are of great importance, as they are pathogenic for humans. The *Yersinia* occur in farm animals, for example pigs and poultry, and on infection can cause a disease in humans. It can therefore be of considerable medical and epidemiological importance to detect, by means of a simple and relatively inexpensive test kit, the course of the chains of infection. This allows conclusions to be drawn about the sources of the pathogens and these can be identified and possibly be made harmless. It is thus possible to detect and differentiate the pathogens of yersinioses.

The results that can be achieved with the detection according to the invention are surprising, because it could not automatically be assumed that the antigens MyfA and/or PsaA are also expressed in sufficient amounts for antibody formation in the human body under real infection conditions. Furthermore, it was not known that specific antibodies of the IgG, IgM and IgA class against MyfA and PsaA antigens are formed in humans.

Based on the relatively high protein homology (44%) between MyfA and PsaA antigens and the already described interspecies homology or interspecies cross-reactivity between non-pathogenic *Yersinia* strains and other enterobacteria, for example *E. coli* and *Salmonella* species, it was not to be expected that the MyfA or the PsaA antigen can be used for differentiating the infective agent. The detection or differentiation is preferably performed with human blood, in particular serum or plasma. Determination is, however, also possible with cerebrospinal fluid or saliva.

In a quite particularly preferred embodiment the sample to be investigated is on the one hand reacted with an antigen selected from the group Yop D, Yop H, Yop M, Yop E, V-AG and Yop-N, quite particularly preferably with Yop D. If this does not result in a positive reaction and otherwise there is no special further suspicion, this can conclude the diagnosis.

Conversely, if the sample to be investigated reacts positively with this antigen, in particular Yop D, in a further diagnostic step the sample to be investigated can be reacted with the antigen PsaA and/or MyfA, preferably with both antigens. Furthermore, it is useful to differentiate the antibodies found, as to whether they are IgG or IgA antibodies. If the IgM or IgA finding is negative, but the IgG finding is positive, presumably an infection has come to an end.

If the IgM or IgA finding, preferably IgA finding, is positive, there may be an acute infection or a secondary disease. The infection is caused by *Yersinia enterocolitica* if the IgG, IgM or IgA reaction, preferably IgG finding, is positive with MyfA. If there is a positive reaction with PsaA, it is an infection with *Yersinia pseudotuberculosis*.

The figures clarify preferred embodiments of the present invention and explain the results obtained in the examples.

FIG. 1 shows the homologous amino acid sequence regions of the MyfA and PsaA antigens. The homologous regions (consensus) are marked in black. A line is drawn round the N- and C-terminal homologous regions.

FIG. 2 explains the in silico determination of the antigenic domains of MyfA and PsaA. The antigenicity index was calculated on the basis of the Jameson-Wolf algorithm and the hydrophilicity of the antigen on the basis of the Kyte-Doolittle algorithm. The so-called leader sequence is marked with a black arrow.

FIG. 3 shows a schematic representation of the DNA sequences of the four His-Tag-MyfA fusion proteins used. The primer sequences used for amplification are marked with arrows (I, II, III, IV). The leader sequences are shown in light-grey and the regions homologous with PsaA are shown in white.

FIG. 4 shows the chromatographic separation (SDS-polyacrylamide-gel electrophoresis) of the MyfA partial fragments myfA 1-441, myfA 121-441 and myfA 121-447 (FIG. 3) with subsequent Coomassie Blue staining (left) and immunoblot (myfA, myfA 1-441, myfA 121-441 and myfA 121-447; FIG. 3) with anti-*Y. enterocolitica* (O:3 or O:9) and anti-MyfA sera from rabbit (right).

FIG. 5 shows verification of the serological reactivity of the purified MyfA total protein (MyfA) and the purified MyfA partial fragments MyfA 1-441, MyfA 121-441 and MyfA 121-447 (FIG. 1; FIG. 3) by means of line-assays. The test strips were incubated with four different anti-*Y. enterocolitica* O:3, O:8 or O:9 sera from rabbit (1-4) before (*) and after infection.

FIG. 6 shows the serological reactivity of human anti-*Y. enterocolitica* or anti-*Y. pseudotuberculosis* serum with YopM, YopH, V-AG, YopD, YopN, YopE, MyfA and PsaA in the line-assay.

FIG. 7 shows the IgG response to Yop, MyfA-MIK and PsaA-MIK antigens with the tested Bavarian blood donor sera (n=40).

FIG. 8 explains the IgG response to Yop, MyfA-MIK and PsaA-MIK antigens with the tested yersiniosis patient sera from Finland (n=18).

FIG. 9 shows the IgG response to Yop, MyfA-MIK and PsaA-MIK antigens with the tested yersiniosis patient sera from Germany (n=23). With the surface protein, YopD is particularly suitable for use in diagnostic testing devices.

EXAMPLE 1

In Silico Determination of the Immunogenic Domains of the MyfA and PsaA Antigens Determination of the homologous antigen regions that might be responsible for the immunogenic reactivity or cross-reactivity of the MyfA and PsaA antigens, was carried out in silico by means of direct amino acid sequence comparison (see FIG. 1). The homologous regions are mainly located in the N- and C-terminus of the MyfA (AA 32-40 and 150-159) and PsaA (AA 29-38 and 149-158) antigen.

The antigenicity index and the hydrophilic character of the antigen regions was determined in silico with the algorithms of Jameson and Wolf (Comput. Appl. Biosci. (1988) p. 181-186) or of Kyte and Doolittle (Kyte and Doolittle, (1982) J. Mol. Biol., 157, p. 105-132) (FIG. 2). The eight >5 AA immunogenic domains of the PsaA antigen are probably located in AA 30-48, 52-56, 59-67, 74-83, 87-96, 122-133, 144-150 and 151-158. The seven putative >5 AA immunogenic domains of the MyfA antigen were localised in AA 35-42, 43-54, 55-73, 79-100, 101-133, 139-148 and 152-159. According to the invention, these fragments are preferably used in the diagnostic tests. However, as the predicative Kyte-Doolittle algorithm is only informative conditionally, the immunogenic epitopes of the new antigens were determined experimentally (Example 2).

Complete Total Protein Sequences:

(Seq ID No. 11)
```
MyfA (159-AA)
AA 1-29: Leader Sequence
AA 30-41: N-terminal fragment (Example 2)
AA 148-159: C-terminal fragment (Example 2)
MNMKKFVKKPLAIAVLMLASGGMVNMVHAEPTVINSKDISATKTVKEGGSFSVEFKATENEI

VSGKLDADTPAFHLVMSDSGEHKGWNVRPTGASEGGQMVSADGTRVDLHTNELSWDND

HWWIDDGSERVEATFFLAAGDEVKAGEYQFTGRVEEYVE
```

(Seq ID No. 12)
PsaA (158-AA)
AA 1-26: Leader Sequence
MKMKCFAKNALAVTTLMIAACGMANASTVINSKDVSGEVTVKQGNTFHVDFAPNTGEIFAG

KQPGDVTMFTLTMGDTAPHGGWRLIPTGDSKGGYMISADGDYVGLYSYMMSWVGIDNNW

YINDDSPKDIKDHLYVKAGTVLKPTTYKFTGRVEEYVF

EXAMPLE 2

Experimental Determination of the Immunogenic Domains of the myfA Antigens
Preparation of the myfA Partial Fragments Four fragments were prepared starting from the complete reading frame of the MyfA antigen (Example 1). Both the complete reading frame including the leader peptide and N-, C-, and N- and C-terminally shortened partial fragments are shown (FIG. 1; FIG. 3).

Specific amplification of the myfA partial fragments was carried out by PCR with chromosomal DNA from *Y. enterocolitica* serotype O:3/4 (*Y. enterocolitica* subsp. *palearctica* strain Y-11; DMSZ 13030) as templates.

The resulting amplificates were cleaved enzymatically with restriction endonucleases and ligated into a suitable vector, pET21-b, which had been cut with the same restriction endonucleases as the amplificates. After transformation of the ligation preparation into a suitable *E. coli* strain, e.g. BL21 pLys, individual clones were tested for the presence of myfA and psaA by agarose-gel electrophoresis of enzymatically cleaved plasmid DNA and then sequenced. In addition, the expression of the partial fragments was identified and characterised by analysis of the expression products by SDS-polyacrylamide-gel electrophoresis with subsequent Coomassie Blue staining or subsequent transfer to nitrocellulose followed by immunological detection. The fusion proteins were purified by Ni-NTA column chromatography according to the manufacturer's information (the company Qiagen).

In addition to the complete reading frame of MyfA (MyfA; FIG. 3), three partial fragments of the antigen were cloned as His-Tag fusion proteins into pET21-b vector. The first fragment (MyfA 1-441) was cloned without the C-terminal region homologous to PsaA (Example 1; FIG. 1) and comprises the AA 1-147 (nucleotide [NT] 1-441). The second fragment (MyfA 121-441) codes for the AA 40-147 (NT 121-441) and therefore does not contain the N- and C-terminal regions homologous to PsaA (Example 1; FIG. 1). The third fragment (MyfA 121-477) codes for the AA 40-159 (NT 121-477) and does not contain the N-terminal sequence of MyfA (Example 1; FIG. 3; FIG. 1).

The following oligonucleotide primers were used for preparing the sequences.

Primer 1 (I):
(Seq ID No. 13)
myfA-f: GTA ATT CCA TAT GAA TAT GAA AAA ATT TGT

Primer 2 (II):
(Seq ID No. 14)
myfA_121f: GTA ATC CCA TAT GGC AAC AAA AAC TGT

Primer 3 (III):
(Seq ID No. 15)
myfA_441rev: TTA CTC GAG TTC ACC TGC TTT AAC

Primer 4 (IV):
(Seq ID No 16)
myfA_rev: ATC TAC TCG AGC TCG ACA TAT TCC TCA A

The following primer combinations were used:

myfA: primer 1 and primer 4
myfA 1-441: primer 1 and primer 3
myfA 121-441: primer 2 and primer 3
myfA 121-477: primer 2 and primer 4

EXAMPLE 3

Verification of Antigenicity

The immunological reactivity/antigenicity of the MyfA fusion proteins (Example 2) was tested by immunoblot (FIG. 4) and line-assay (FIG. 5)

FIG. 4, left, shows in each case cell lysates (ZL) of MyfA total protein (MyfA, including leader sequence; Example 1; FIG. 1; Example 2; FIG. 3) and/or *E. coli* BL21 pLys cells expressing one of the three MyfA partial fragments (MyfA 1-441, MyfA 121-441 and MyfA 121-447) and the His-tagged recombinant MyfA proteins (MyfA 1-441, MyfA 121-441 and MyfA 121-447) purified by Ni-NTA column chromatography.

FIG. 4, right, shows an immunoblot with two anti-*Y. enterocolitica O:*3 or O:9 sera and an anti-MyfA serum from rabbit. The MyfA-protein shortened on the N- and C-terminus (MyfA 121-441; Example 1; FIG. 1; Example 2; FIG. 3) does not show any reaction with the sera used. The protein shortened on the C-terminus MyfA 1-441 (FIG. 1; FIG. 2) shows a weaker reaction than the protein shortened on the N-terminus MyfA 121-447 (FIG. 1; FIG. 2). Therefore the C-terminus appears to contain a particularly important immunogenic region, but the N-terminus is also diagnostically important.

The proteins could be detected by detecting the His-tags with a nickel-NTA conjugate from rabbit (very weak reaction, no double bands). The immunoblot with an anti-*Y. pseudotuberculosis* serum from rabbit did not show any reaction.

The immunological reactivity/antigenicity of the purified MyfA total protein (MyfA) and of the purified MyfA partial fragments MyfA 1-441, MyfA 121-441 and MyfA 121-447 (Example 1, FIG. 1; Example 2; FIG. 3) was verified by means of line-assays (FIG. 5). The test strips were incubated with four different anti-*Y. enterocolitica* sera from rabbit (serum 1 and 4: serotype O:3; serum 2: serum O:9, serum 3: O:8) before (*) and after experimental peroral infection with precultured *Yersinia*. Recombinantly produced YopD and YopH antigens were incorporated into the assay as immunisation or assay control. Additionally, so as to be able to evaluate the cross-reactivity of the MyfA and PsaA antigens, recombinantly produced PsaA antigen was also included in the assay (FIG. 5). The reactivity of the antigens was in addition verified with an anti-*Y. pseudotuberculosis* serum from rabbit.

The blood samples taken before infection showed no reactivity with the antigens of the assay (i.e. YopD, YopH, MyfA, MyfA 1-441, MyfA 121-441, MyfA 121-447, PsaA). After the experimental infection, all four samples reacted with the *Yersinia*-specific antigens YopD and YopH (FIG. 5). As already shown in the immunoblot (FIG. 4), the C- (Δ C-terminus) or the N- and C- (Δ N- and C-terminus) terminally shortened MyfA protein showed markedly reduced reactivity and the N-terminally shortened protein (Δ N-terminus) reduced reactivity in comparison with the MyfA total protein (FIG. 5). Interestingly, sera No. 2 (very weakly), 3 (weakly) and 4 (positively) also reacted with the applied PsaA antigen. The anti-*Y. pseudotuberculosis* serum from rabbit reacted very strongly with YopD and PsaA, but showed no reactivity with the total antigen MyfA or its partial fragments. The cross-reactivity of the anti-*Y. enterocolitica* sera with PsaA occurring in the assay is possibly caused by semi-optimum production conditions (i.e. purification via His-Taq, buffer conditions or antigen concentration too high). In addition, cross-reactivities occurring between MyfA and PsaA or other *Yersinia* surface proteins (so-called RPs) are known in rabbit sera immunised with precultured *Yersinia* (Leiva et al., Heesemann et al.). For the subsequent experiments, the MyfA and PsaA antigens were recloned (without His-Taq and leader sequence), purified and the assay conditions were optimised (Examples 3-5).

EXAMPLE 4

Preparation and Purification of the Recombinant MyfA and PsaA Antigens

MyfA (pmyfA MIK) and PsaA (ppsaA-MIK) expression clones were prepared starting from the complete reading frames (Example 1) of the two antigens. The following oligonucleotide primers were used for preparation of the sequences. The proteins were prepared without leader sequence (MyfA AA 1-29 and PsaA AA 1-26; Example 1), as preliminary experiments had shown that the leader peptide causes reduced expression.

```
pmyfA-MIK
Primer 5 (Seq ID No. 17):
myfA-F-NdeI: CAC ATA TGG AAC CGA CTG TTA TTA ATA

GTA AAG ACA TC

Primer 6 (Seq ID No. 18):
myfA-R-BamI: ATG GAT CCT TAC TCG ACA TAT TCC TCA

ACA CG ppsaA-MIK
Primer 7 (Seq ID No. 19):
psaA-F-NdeI: GCC ATA TGT CTA CTG TCA TTA ACT CCA

AGG ATG

Primer 8 (Seq ID No. 20):
psaA-R-BamI: CAG GAT CCT TAA AAT ACA TAC TCT TCA

ACA CGC C
```

Specific amplification of the myfA fragment was performed by PCR with chromosomal DNA from *Y. enterocolitica* serotype O:3/4 (*Y. enterocolitica* subsp. *palearctica* strain Y-11; DMSZ 13030) as template. The psaA fragment was amplified with chromosomal DNA from *Y. pseudotuberculosis* serotype 1A.

The resulting amplificates were enzymatically cleaved with restriction endonucleases Nde I and Bam HI and were ligated into a suitable vector, pET3c (New England Biolabs). After transformation of the ligation preparation into the *E. coli* strain UT 5600 (Elish et al. [1998] J. Gen. Microbiol., 134, p. 1355-1364) the clones were tested for the presence of the myfA and psaA fragments by agarose-gel electrophoresis of enzymatically cleaved plasmid DNA and by DNA sequencing (see below). In addition, the expression of the antigens was identified and characterised by analysis of the expression products MyfA-MIK and PsaA-MIK by SDS-polyacrylamide-gel electrophoresis followed by Coomassie Blue staining or subsequent transfer to nitrocellulose followed by immunological detection.

The recombinant proteins MyfA-MIK and PsaA-MIK were purified by anion-exchange and cation-exchange column chromatography. An anion exchange (Q-Sepharose Fast Flow; GE Healthcare, Munich, Germany) was performed in the first step, a cation exchange (S-Source 15; GE Healthcare) in the second step and an anion exchange (Q-Source 30; GE Healthcare) in the third step. The individual purification steps and/or the purified protein were verified by SDS-polyacrylamide-gel electrophoresis with subsequent Coomassie Blue staining or subsequent transfer to nitrocellulose followed by immunological detection and were characterised with respect to the degree of purity, possible protein cleavage and immunological reactivity.

EXAMPLE 5

DNA Sequencing of the pmyfA-MIK and ppsaA-MIK Expression Clones and Resultant Protein Sequences (AA) MyfA-MIK and PsaA-MIK The START (atg) and STOP (uaa) codons are marked in black.

DNA Sequences

```
of pmyfA-MIK (396 bp) (Seq ID No. 21):
atggaaccgactgttattaatagtaaagacatctctgcaacaaaaactgttaaagagggaggttcgttctcagttgaattcaaggc cactgaaaacgagattgtgtcaggcaaattggatgcagatacacctgccttccatctggtaatgtcggactcaggggaacataaa ggttggaatgttcggcctaccggtgcatctgagggaggacagatggtttctgcagatggtaccagagttgacttacatacaaatga gctatcgtgggataacgaccactggtggatagatgacggttctgagcgtgtggaagcgactttcttctgctgctggcgacgagg ttaaagcaggtgaatatcagttcactgggcgtgttgaggaatatgtcgagtaa ppsaA-MIK (402 bp) (Seq ID No. 22):
atgtctactgtcattaactccaaggatgtttctggtgaggtgactgtcaagcagggaaacacattccacgtcgattttgcgcctaa cacaggagagatttttgcgggtaaacagccgggtgatgtcactatgtttacgctaactatgggtgatactgcaccacacggtggtt ggcgtttgattccaacaggggactcaaaaggtggatatatgatcagcgccgatggtgactatgttggtttatacagttatatgatg tcatgggtaggtatagataataactggtatataaatgatgactctcctaaagatataaaagatcatctgtacgttaaggcagggac tgtccttaaaccaacgacttataaattcacggggcgtgttgaagagtatgtattttaa
```

Amino acid sequences (AA)

MyfA-MIK (132-AA)
(Seq ID No. 23)
MEPTVINSKDISATKTVKEGGSFSVEFKATENEIVSGKLDADTPAFHL
VMSDSGEHKGWNVRPTGASEGGQMVSADGTRVDLHTNELSWDNDHWWI
DDGSERVEATFFLAAGDEVKAGEYQFTGRVEEYVE.

PsaA-MIK (134-AA)
(Seq ID No. 24)
MSTVINSKDVSGEVTVKQGNTFHVDFAPNTGEIFAGKQPGDVTMFTLT
MGDTAPHGGWRLIPTGDSKGGYMISADGDYVGLYSYMMSWVGIDNNW
YINDDSPKDIKDHLYVKAGTVLKPTTYKFTGRVEEYVF.

EXAMPLE 6

Serological Differentiation of Yersinioses Caused by *Y. enterocolitica* or *Y. pseudotuberculosis*

Two human serum samples were defined by Widal reaction as anti-*Y. enterocolitica* serotype O:3 (LYE16)- or as anti-*Y. pseudotuberculosis* (LYE01)-IgG-positive.

Comparison of the serological IgG reactivity of Yop, MyfA-MIK and PsaA-MIK antigens (Example 3) by means of line-assays showed that the *Y. pseudotuberculosis*-positive serum sample reacted very strongly with YopD and PsaA. In contrast, the anti-*Y. enterocolitica*-IgG-positive sample reacted with the antigens YopM, YopH, V-AG, YopD, YopN, YopE and MyfA. This serum sample also showed very weak reactivity with PsaA.

There is thus an indication that the antigens MyfA-MIK and PsaA-MIK make possible the serological differentiation of *Y. enterocolitica* and *Y. pseudotuberculosis* infections.

EXAMPLE 7

Comparison of the Serological Prevalence of the Anti-Yop, Anti-MyfA and Anti-PsaA Antibodies of the IgG, IgM and IgA Class in Serum Samples from Bavarian Blood Donors or in Serum Samples from Finnish and German Yersiniosis Patients The IgG, IgM and IgA response to recombinantly produced YopM, YopH, V-AG, YopD, YopN, YopE, MyfA-MIK and PsaA-MIK (Example 4 and 5) antigens with sera from three different sera collections (i.e. Bavarian blood donors n=40; Bavaria; Germany, yersiniosis patients from Finland [KTL, n=18] and yersiniosis patients from Germany [YeD, n=23]) were investigated by line-assays. The recomLine *Yersinia* from the company Microgen GmbH was used as reference test.

Blood Donor Sera

48% (n=19) of the tested blood donor sera from Bavaria (n=40) showed IgG reactivity with YopD (FIG. 7; Table 1). Eight serum samples had an IgG response, which was not directed against YopD but exclusively against YopH (n=4), YopH and YopN (n=1), YopH and V-AG (n=1), YopM (n=1) and PsaA-MIK (n=1). Three of the samples reacted with the two new *Yersinia* antigens MyfA-MIK (n=4) and PsaA-MIK (n=9; Table 1).

As the sera were obtained from healthy donors, IgM antibodies to YopD could not be detected in any of the sera tested (Table 1). Three Yop-IgG-positive sera (n=19) had an isolated IgM titre directed against YopH (n=2; 11%; serum No. 1087: high IgG titre against YopD and PsaA; serum No. 1099: high IgG titre against YopD) or PsaA (n=1; 5%, serum No. 1083: high IgG titre against YopD, MyfA-MIK and PsaA-MIK). None of the samples tested reacted with MyfA-MIK (Table 1).

Seven YopD-IgG-positive serum samples from blood donors (n=19) showed an IgA titre against YopD (Table 1). Three of the sera tested reacted with PsaA-MIK. Interestingly, the Yop-IgG-negative serum sample No. 1080 showed a very weak isolated reactivity with PsaA. The YopD and PsaA-MIK IgG-high positive serum samples No. 1096 and No. 1110 also had a strong (serum No. 1096) or weak (serum No. 1110) IgA response to PsaA-MIK (Table 1). None of the samples tested reacted with MyfA-MIK (Table 1). Based on the parallel occurrence of anti-IgA-reactivity to the YopD, Yop-N and PsaA antigens in the samples No. 1110, it is to be expected that this is a diagnostically relevant serological finding, for example recent *Y. pseudotuberculosis* infection or occurrence of reactive arthritis.

Sera of Yersiniosis Patients from Finland 17 (90%) of the sera tested from patients with suspected *Yersinia*-induced reactive arthritis from Finland (n=18) showed an IgG response to YopD (FIG. 8; Table 2). Eleven of the samples reacted with MyfA-MIK (65%) and four with PsaA-MIK (24%) (FIG. 8; Table 2).

15 (88%) of the sera tested had IgM antibodies to YopD (Table 2). One serum (No. 52) also showed a strong IgM response to PsaA-MIK (Table 2).

17 serum samples from yersiniosis patients (n=18) had an IgA titre against YopD (Table 2). Three of the sera tested also reacted with PsaA-MIK (No. 23, 24 and 40; Table 2).

Sera of Yersiniosis Patients from Germany

All (n=23) sera tested of yersiniosis patients from Germany showed an IgG reactivity with YopD (FIG. 9; Table 3). 15 serum samples (65%) additionally had an IgG response to PsaA-MIK. Four (17%) of the samples reacted with the antigen MyfA-MIK (FIG. 9; Table 3). Interestingly, two of the serum samples (serum 1038 and 1025) reacted with the two antigens MyfA-MIK and PsaA-MIK. However, the IgG response to MyfA-MIK was much weaker compared with PsaA-MIK (Table 3).

A low IgM response to YopD was only detected in two (9%) of the sera tested (n=23), and to YopE in three sera (Table 3). One serum, No. 986, reacted very strongly with PsaA-MIK (Table 3).

All sera tested from yersiniosis patients had an IgA response to YopD (Table 3). One of the samples also reacted with MyfA-MIK (serum No. 976) and another with PsaA-MIK (serum No. 1025). These sera also showed a strong IgG response to MyfA-MIK or PsaA-MIK (Table 3).

Interestingly, the two tested collections of samples from yersiniosis patients from Finland and Germany differ in anti-MyfA- and anti-PsaA-IgG prevalence. Owing to low isolation rate or technically difficult cultivation and isolation of the *Y. pseudotuberculosis* strains, at present no reliable epidemiological data are available.

TABLE 1

The IgG, IgM and IgA response to recombinantly produced YopM, YopH, V-AG, YopD, YopN, YopE, MyfA-MIK and PsaA-MIK antigens among the tested blood donor sera from Bavaria (n = 40).

| Serum | YopM | YopH | V-AG | YopD | YopN | YopE | MyfA | PsaA |
|---|---|---|---|---|---|---|---|---|
| IgG response | | | | | | | | |
| 1075 | 1 | 4 |  | 4 |  | 2 | 4 | 4 |
| 1076 |  | 1 |  |  | 1 |  |  |  |
| 1077 |  | 2 |  | 4 |  | 4 | 2 |  |
| 1078 |  |  |  |  |  |  |  |  |
| 1079 |  |  |  |  |  |  |  |  |
| 1080 |  |  |  |  |  |  |  |  |
| 1081 |  |  |  |  |  |  |  |  |
| 1082 |  | 1 |  | 3 |  |  |  |  |
| 1083 |  |  |  | 4 | 1 |  | 4 | 2 |
| 1084 |  |  |  |  |  |  |  |  |
| 1085 |  | 3 |  | 1 |  |  |  |  |
| 1086 |  | 3 |  | 3 |  |  |  |  |
| 1087 |  |  |  | 4 |  |  |  | 4 |
| 1088 |  |  |  |  |  |  |  |  |
| 1089 |  |  |  |  |  |  |  |  |
| 1090 |  | 2 |  |  |  |  |  |  |
| 1091 |  | 2 |  |  |  |  |  |  |
| 1092 |  |  |  |  |  |  |  |  |
| 1093 | 2 | 1 |  | 4 |  |  |  |  |
| 1094 |  |  |  |  |  |  |  | 2 |
| 1095 |  |  |  |  |  |  |  |  |
| 1096 |  |  |  | 3 |  |  | 3 | 4 |
| 1097 |  | 1 |  | 3 |  |  |  |  |
| 1098 |  | 1 |  | 1 |  |  |  |  |
| 1099 |  |  |  | 3 |  |  |  |  |
| 1100 |  |  |  |  |  |  |  |  |
| 1101 | 1 | 3 |  | 2 |  |  |  |  |
| 1102 |  | 3 |  | 2 |  |  |  | 3 |
| 1103 |  | 3 |  |  |  |  |  |  |
| 1104 |  | 1 |  |  |  |  |  |  |
| 1105 |  |  |  |  |  |  |  |  |
| 1106 |  |  |  |  |  |  |  |  |
| 1107 | 1 |  |  |  |  |  |  |  |
| 1108 |  |  |  | 1 |  |  |  | 3 |
| 1109 |  | 2 |  | 2 | 2 |  |  |  |
| 1110 |  |  |  | 2 |  |  |  | 3 |
| 1111 |  |  |  |  |  |  |  |  |
| 1112 |  | 2 |  | 4 |  |  |  | 2 |
| 1113 |  | 2 | 2 |  |  |  |  |  |
| 1114 |  |  |  | 4 |  |  |  |  |
| IgM response | | | | | | | | |
| 1075 |  |  |  |  |  |  |  |  |
| 1076 |  |  |  |  |  |  |  |  |
| 1077 |  |  |  |  |  |  |  |  |
| 1078 |  |  |  |  |  |  |  |  |
| 1079 |  |  |  |  |  |  |  |  |
| 1080 |  |  |  |  |  |  |  |  |
| 1081 |  |  |  |  |  |  |  |  |
| 1082 |  |  |  |  |  |  |  |  |
| 1083 |  |  |  |  |  |  |  | 2 |
| 1084 |  |  |  |  |  |  |  |  |
| 1085 |  |  |  |  |  |  |  |  |
| 1086 |  |  |  |  |  |  |  |  |
| 1087 |  | 1 |  |  |  |  |  |  |
| 1088 |  |  |  |  |  |  |  |  |
| 1089 |  |  |  |  |  |  |  |  |
| 1090 |  |  |  |  |  |  |  |  |
| 1091 |  |  |  |  |  |  |  |  |
| 1092 |  |  |  |  |  |  |  |  |
| 1093 |  |  |  |  |  |  |  |  |
| 1094 |  |  |  |  |  |  |  |  |
| 1095 |  |  |  |  |  |  |  |  |
| 1096 |  |  |  |  |  |  |  |  |
| 1097 |  |  |  |  |  |  |  |  |
| 1098 |  |  |  |  |  |  |  |  |
| 1099 |  | 4 |  |  |  |  |  |  |
| 1100 |  |  |  |  |  |  |  |  |
| 1101 |  |  |  |  |  |  |  |  |
| 1102 |  |  |  |  |  |  |  |  |
| 1103 |  |  |  |  |  |  |  |  |
| 1104 |  |  |  |  |  |  |  |  |

TABLE 1-continued

The IgG, IgM and IgA response to recombinantly produced YopM, YopH, V-AG, YopD, YopN, YopE, MyfA-MIK and PsaA-MIK antigens among the tested blood donor sera from Bavaria (n = 40).

| Serum | YopM | YopH | V-AG | YopD | YopN | YopE | MyfA | PsaA |
|---|---|---|---|---|---|---|---|---|
| 1105 | | | | | | | | |
| 1106 | | | | | | | | |
| 1107 | | | | | | | | |
| 1108 | | | | | | | | |
| 1109 | | | | | | | | |
| 1110 | | | | | | | | |
| 1111 | | | | | | | | |
| 1112 | | | | | | | | |
| 1113 | | | | | | | | |
| 1114 | | | | | | | | |
| IgA response | | | | | | | | |
| 1075 | | | | | | | | |
| 1076 | | | | | | | | |
| 1077 | | | | | 1 | | | |
| 1078 | | | | | | | | |
| 1079 | | | | | | | | |
| 1080 | | | | | | | | 1 |
| 1081 | | | | | | | | |
| 1082 | | | | | 1 | | | |
| 1083 | | | | | | | | |
| 1084 | | | | | | | | |
| 1085 | | | | | | | | |
| 1086 | | | | | | | | |
| 1087 | | | | | 4 | | | |
| 1088 | | | | | | | | |
| 1089 | | | | | | | | |
| 1090 | | | | | | | | |
| 1091 | | | | | | | | |
| 1092 | | | | | | | | |
| 1093 | | | | | 1 | | | |
| 1094 | | | | | | | | |
| 1095 | | | | | | | | |
| 1096 | | | | | | | | | 3 |
| 1097 | | | | | 3 | | | |
| 1098 | | | | | | | | |
| 1099 | | | | | | | | |
| 1100 | | | | | | | | |
| 1101 | | | | | | | | |
| 1102 | | | | | | | | |
| 1103 | | | | | | | | |
| 1104 | | | | | | | | |
| 1105 | | | | | | | | |
| 1106 | | | | | | | | |
| 1107 | | | | | | | | |
| 1108 | | | | | | | | |
| 1109 | | | | | | | | |
| 1110 | | | | | 3 | 2 | | 1 |
| 1111 | | | | | | | | |
| 1112 | | | | | | | | |
| 1113 | | | | | | | | |
| 1114 | | | | | 1 | | | |

The reactivity was assessed semi-quantitatively with the following assessment scheme:
1 = very weak reactivity,
2 = weak reactivity,
3 and 4 = strong reactivity.

TABLE 2

The IgG, IgM and IgA response to recombinantly produced YopM, YopH, V-AG, YopD, YopN, YopE, MyfA-MIK and PsaA-MIK antigens among the tested yersiniosis patient sera from Finland (n = 18).

| | YopM | YopH | V-AG | YopD | YopN | YopE | MyfA | PsaA |
|---|---|---|---|---|---|---|---|---|
| IgG response | | | | | | | | |
| 1 | 1 | 3 | 3 | 4 | 2 | 3 | 1 | |
| 5 | 2 | 4 | 1 | 4 | | 1 | 3 | |
| 6 | | 1 | 1 | 4 | | | | |
| 11 | | 3 | 1 | 3 | | 2 | 1 | |
| 16 | | 2 | 2 | 3 | | | | |
| 19 | | 3 | | 4 | | 2 | | |
| 23 | | 2 | | 3 | | | | 3 |
| 24 | 2 | 4 | 3 | 4 | | 3 | 1 | 4 |

TABLE 2-continued

The IgG, IgM and IgA response to recombinantly produced YopM, YopH, V-AG, YopD, YopN, YopE, MyfA-MIK and PsaA-MIK antigens among the tested yersiniosis patient sera from Finland (n = 18).

| | YopM | YopH | V-AG | YopD | YopN | YopE | MyfA | PsaA |
|---|---|---|---|---|---|---|---|---|
| 34 | | 3 | | 3 | | | 1 | 2 |
| 35 | 2 | 3 | 3 | 4 | | 1 | | |
| 36 | 2 | 2 | 2 | 4 | | | 1 | 1 |
| 40 | 3 | 3 | 3 | 4 | 1 | 2 | 3 | 1 |
| 44 | | 3 | 1 | 3 | | 1 | | |
| 47 | | | | | | | | |
| 50 | 2 | 3 | | 4 | | 3 | 1 | 2 |
| 51 | 3 | 4 | 3 | 4 | 3 | 3 | 1 | |
| 52 | 1 | 4 | 2 | 4 | 2 | 3 | 1 | |
| 53 | 3 | 4 | 2 | 4 | | | 1 | |
| IgM response | | | | | | | | |
| 1 | | 1 | | 4 | | | | |
| 5 | | | | 3 | | | | |
| 6 | | | | 2 | | | | |
| 11 | | | | 1 | | | | |
| 16 | | | | 1 | | | | |
| 19 | | | | 3 | | | | |
| 23 | | | | | | | | |
| 24 | | | | 3 | | | | |
| 34 | | | | | | | | |
| 35 | | | | 4 | | | | |
| 36 | | | | 3 | | | | |
| 40 | | | | 1 | | | | |
| 44 | | | | 2 | | | | |
| 47 | | | | | | | | |
| 50 | | | | 1 | | | | |
| 51 | | | | 3 | | | | |
| 52 | | | | 2 | | | | 3 |
| 53 | | | | 4 | | | | |
| IgA response | | | | | | | | |
| 1 | | | | 2 | | | | |
| 5 | | | | 2 | | | | |
| 6 | | | | 4 | | | | |
| 11 | | | | 1 | | | | |
| 16 | | | | 2 | | | | |
| 19 | | | | 2 | | | | |
| 23 | | | | 2 | | | | 4 |
| 24 | | 1 | | 4 | | | | 3 |
| 34 | | | | 2 | | | | |
| 35 | | | | 3 | | | | |
| 36 | | | | 3 | | | | |
| 40 | 1 | 2 | 1 | 4 | 2 | 2 | | 1 |
| 44 | | 1 | | 4 | | | | |
| 47 | | | | | | | | |
| 50 | | | | 3 | | | | |
| 51 | | 1 | | 2 | | | | |
| 52 | | | | 2 | 1 | | | |
| 53 | | 3 | | 4 | | | | |

The reactivity was assessed semi-quantitatively with the following assessment scheme:
1 = very weak reactivity,
2 = weak reactivity,
3 and 4 = strong reactivity.

TABLE 3

The IgG, IgM and IgA response to recombinantly produced YopM, YopH, V-AG, YopD, YopN, YopE, MyfA-MIK and PsaA-MIK antigens among the tested yersiniosis patient sera from Germany (n = 23).

| | YopM | YopH | V-AG | YopD | YopN | YopE | MyfA | PsaA |
|---|---|---|---|---|---|---|---|---|
| IgG response | | | | | | | | |
| 262 | | | | 2 | | | | 2 |
| 327 | | 4 | 2 | 4 | 3 | 2 | | 2 |
| 1534 | 1 | 3 | 3 | 4 | 1 | 4 | 3 | |
| 976 | | 4 | | 4 | | 4 | 2 | |
| 1038 | 2 | 3 | 2 | 3 | | | 1 | 2 |
| 158 | 2 | 3 | 1 | 4 | | 2 | | 3 |
| 58 | 2 | 3 | | 4 | | | | |
| 321 | | | | 4 | | | | 2 |
| 326 | | 4 | 2 | 4 | 2 | 2 | | 2 |
| 333 | | | 1 | 4 | | | | 2 |
| 1025 | | 3 | | 4 | | | 1 | 4 |
| 1547 | | | | 1 | | | | |
| 111 | | | | 4 | | | | 2 |
| 1 | 3 | 4 | 3 | 4 | | 4 | | 3 |
| 252 | 1 | 4 | 2 | 4 | 2 | 4 | | |
| 262 | | | | 3 | | | | 3 |
| 113 | | 4 | 2 | 4 | | 3 | | |
| 986 | | 4 | | 4 | | | | |
| 320 | 2 | | | 2 | | | | |
| 1748 | 1 | | 1 | 4 | | | | 3 |
| 1176 | | 3 | | 3 | | | | 3 |
| 1801 | | | | 4 | | | | 3 |
| 1810 | | | | 4 | | | | 3 |
| IgM response | | | | | | | | |
| 262 | | | | | | | | |
| 327 | | | | | | | | |
| 1534 | | | | | | | | |
| 976 | | | | | | | | |
| 1038 | | | | | | 1 | | |

TABLE 3-continued

The IgG, IgM and IgA response to recombinantly produced YopM, YopH, V-AG, YopD, YopN, YopE, MyfA-MIK and PsaA-MIK antigens among the tested yersiniosis patient sera from Germany (n = 23).

|      | YopM | YopH | V-AG | YopD | YopN | YopE | MyfA | PsaA |
|------|------|------|------|------|------|------|------|------|
| 158  |      |      |      |      |      | 1    |      |      |
| 58   |      |      |      |      |      | 1    |      |      |
| 321  |      |      |      | 1    |      |      |      |      |
| 326  |      |      |      |      |      |      |      |      |
| 333  |      |      |      | 1    |      |      |      |      |
| 1025 |      |      |      |      |      |      |      |      |
| 1547 |      |      |      |      |      |      |      |      |
| 111  |      |      |      |      |      |      |      |      |
| 1    |      |      |      |      |      |      |      |      |
| 252  |      |      |      |      |      |      |      |      |
| 262  |      |      |      |      |      |      |      |      |
| 113  |      |      |      |      |      |      |      |      |
| 986  |      |      |      |      |      |      |      | 4    |
| 320  |      |      |      |      |      |      |      |      |
| 1748 |      |      |      |      |      |      |      |      |
| 1176 |      |      |      |      |      |      |      |      |
| 1801 |      |      |      |      |      |      |      |      |
| 1810 |      |      |      |      |      |      |      |      |
| *IgA response* | | | | | | | | |
| 262  |      |      |      | 2    |      |      |      |      |
| 327  |      |      |      | 2    |      |      |      |      |
| 1534 |      |      |      | 2    |      |      |      |      |
| 976  |      |      |      | 2    |      | 1    |      |      |
| 1038 |      |      |      | 2    |      |      |      |      |
| 158  |      |      |      | 3    |      |      |      |      |
| 58   |      |      |      | 2    |      |      |      |      |
| 321  |      |      |      | 3    |      |      |      |      |
| 326  |      |      |      | 2    |      |      |      |      |
| 333  |      |      |      | 3    |      |      |      |      |
| 1025 |      |      |      | 2    |      |      |      | 3    |
| 1547 |      |      |      | 1    |      |      |      |      |
| 111  |      |      |      | 3    |      |      |      |      |
| 1    | 3    |      | 3    | 3    |      |      |      |      |
| 252  |      |      |      | 2    |      |      |      |      |
| 262  |      |      |      | 3    |      |      |      |      |
| 113  |      |      |      | 3    |      |      |      |      |
| 986  |      |      |      | 2    |      |      |      |      |
| 320  | 2    |      |      | 1    |      |      |      |      |
| 1748 |      |      |      | 3    |      | 2    |      |      |
| 1176 |      |      |      | 4    |      |      |      |      |
| 1801 |      |      |      | 4    |      |      |      |      |
| 1810 |      |      |      | 4    |      |      |      |      |

The reactivity was assessed semi-quantitatively with the following assessment scheme:
1 = very weak reactivity,
2 = weak reactivity,
3 and 4 = strong reactivity.

EXAMPLE 8

Diagnostic Relevance of the PsaA-MIK and MyfA-MIK Antigens in the Diagnosis of Acute *Y. pseudotuberculosis* Infections The abbreviation "MIK" indicates that the antigens are produced recombinantly by the applicant.

The PsaA-MIK and MyfA-MIK antigens were used in a bead-based assay system (Luminex) for detecting IgG, IgM and IgA reactivity to the PsaA-MIK or the MyfA-MIK antigen. A collection of serum samples from patients who had acute yersiniosis caused by *Yersinia pseudotuberculosis* (K. Jalava, P. Nuorti: "Porkkanaraasteesta laaja *Yersinia pseudotuberculosis*-epidemia, Kansanterveyslehti, 2003) was used. Eight *Y. enterocolitica* IgG-positive (determined with so-called Widal haemagglutination test and a blot assay) and 19 *Y. enterocolitica*-negative routine samples were used as negative comparison group. The results are presented in Table 4.

96.9% (63 samples from 65 samples tested) of the tested *Y. pseudotuberculosis* patient samples showed high IgG reactivity to the PsaA-MIK antigen. Only three of the samples tested reacted in parallel to both antigens (MyfA-MIK and PsaA-MIK). 44.6% of the samples had anti-PsaA-MIK-IgM reactivity and 58.5% of the samples had anti-PsaA-MIK-IgA reactivity. None of the samples tested reacted with the MyfA-MIK antigen when antibodies of the IgM and IgA classes were investigated.

75.0% of the *Y. enterocolitica* WIDAL-positive and blot-positive samples were IgG-positive for the MyfA-MIK antigen. None of these samples reacted with the PsaA-MIK antigen. None of these samples showed IgM or IgA reactivity to the PsaA-MIK or MyfA-MIK antigens.

None of the *Yersinia* IgG-negative samples (n=19) reacted with the PsaA-MIK antigen. Three of the samples showed isolated anti-MyfA-MIK-IgG reactivity and two of the samples showed isolated anti-PsaA-MIK-IgM reactivity.

TABLE 4

Investigation of anti-PsaA-MIK and -MyfA-MIK IgG, IgM and IgA reactivity in patients with yersiniosis caused by *Y. pseudotuberculosis* and in *Y. enterocolitica*-IgG - positive or *Yersinia*-IgG - negative samples.

| Sample collection | IgG PsaA | IgG MyfA | IgM PsaA | IgM MyfA | IgA PsaA | IgA MyfA |
|---|---|---|---|---|---|---|
| *Y. pseudo-tuberculosis*-patients' samples n = 65 | 63 (96.9%) | 3 (4.6%) | 29 (44.6%) | 0 | 38 (58.5%) | 0 |
| *Y. enterocolitica* IgG - positive n = 8 | 0 | 6 (75.0%) | 0 | 0 | 0 | 0 |
| *Yersinia* IgG - negative n = 19 | 0 | 3 (15.8%) | 2 (10.5%) | 0 | 0 | 0 |

The present example provides evidence that, surprisingly, the antigens PsaA or MyfA make it possible to differentiate infections with *Y. pseudotuberculosis* from infections with *Y. enterocolitica*, although there are relatively high homologies between the two antigens, which can also lead to cross-reactivities. Cross-reactivities to MyfA-like or PsaA-like antigens, which occur in other enterobacteria, can be ruled out through the use of the other antigens described here, in particular Yop D.

Based on these results it is to be assumed that the device described here could also be used for serologically detecting an infection caused by *Y. pestis*. However, because a *Y. pestis* infection—in contrast to a *Y. pseudotuberculosis* infection—is typically associated with a black, rapidly progressing, symptomatology with a different course (so-called pneumonic plague, bubonic plague), serodiagnosis supported by clinical symptomatology permits reliable differentiation of the two types of infection.

---

The invention claimed is:

1. A device for serologically differentiating an infection with *Yersinia enterocolitica* from an infection with *Yersinia pseudotuberculosis*, wherein said device comprises (a) at least one antigen of a first group selected from the group consisting of: (i) YopD, (ii) YopH, (iii) YopM, (iv) YopE, (v) V-AG, (vi) YopN and (vii) fragments thereof having at least eight consecutive amino acids and at least one diagnostically relevant epitope, and (b) at least one antigen of a second group selected from the group consisting of: (i) MyfA, (ii) PsaA, and (iii) fragments thereof having at least eight consecutive amino acids and at least one diagnostically relevant epitope, wherein each individual first and second group antigen is fixed to the device in a spatially separated manner.

2. The device according to claim 1, further wherein said device comprises both the MyfA protein or fragment thereof, and the PsaA protein or fragment thereof, wherein said fragments comprise at least eight consecutive amino acids and at least one diagnostically relevant epitope as set forth in claim 1.

3. The device according to claim 1, further wherein said device comprises the YopD antigen or a fragment thereof having at least eight consecutive amino acids as set forth in claim 1.

4. The device according to claim 1, further wherein the fragments of the proteins used as first and second group antigens comprise at least 12 consecutive amino acids of the respective antigen.

5. The device according to claim 1, further wherein the fragments of the proteins used as first and second group antigens comprise at least 20 consecutive amino acids of the respective antigen.

6. The device according to claim 1, further wherein the fragments of the proteins used as first and second group antigens comprise at least 30 amino acids of the respective antigen.

7. The device according to claim 1, wherein said device comprises a diagnostic kit.

8. The device according to claim 7, wherein said kit comprises an ELISA assay in which each first and second group antigen is individually bound to a carrier matrix in a spatially separated manner.

9. The device according to claim 7, wherein said kit comprises a line-test in which each first and second group antigen is individually bound to one or more test strips in a spatially separated manner according to a predetermined pattern.

10. The device according to claim 7, wherein said kit comprises immunoblots, bead-based assays or microarrays in which each first and second group antigen is individually immobilized to one or more substrates in a spatially separated manner.

11. A method of preparing a device for serologically differentiating an infection caused by *Yersinia enterocolitica* from an infection caused by *Yersinia pseudotuberculosis*, comprising the steps of:
   a. providing at least one second group antigen selected from the group consisting of: (i) MyfA, (ii) PsaA and (iii) fragments thereof comprising at least 8 consecutive amino acids and at least one diagnostically relevant epitope; and
   b. providing at least one first group antigen selected from the group consisting of: (i) Yop D, (ii) Yop H, (iii) Yop M, (iv) Yop E, (v) V-AG, (vi) Yop N and (vii) fragments thereof having at least 8 consecutive amino acids and at least one diagnostically relevant epitope,
   c. fixing each of said first and second group antigens to the device in a spatially separated manner.

12. A method of serologically differentiating infection in a subject caused by *Yersinia enterocolitica* from an infection caused by *Yersinia pseudotuberculosis*, said method comprising the step of reacting a serum sample obtained from said subject with the device of claim 1, wherein a positive sample reaction with at least one antigen of the first group is indicative of *Yersinia* infection, a positive sample reaction with an antigen of the second group comprising MyfA or a fragment thereof is indicative of *Yersinia enterocolitica* infection and a positive sample reaction with an antigen of the second group comprising PsaA or a fragment thereof is indicative of *Yersinia pseudotuberculosis* infection.

* * * * *